United States Patent [19]

Iizuka et al.

[11] Patent Number: 4,863,904

[45] Date of Patent: Sep. 5, 1989

[54] DIPEPTIDES AS RENIN INHIBITORS

[75] Inventors: Kinji Iizuka; Tetsuhide Kamijo; Tetsuhiro Kubota, all of Nagano; Kenji Akahane, Tokyo; Hideaki Umeyama, Chiba; Yoshiaki Kiso, Osaka, all of Japan

[73] Assignee: Kissei Pharmaceutical Co., Ltd., Nagano, Japan

[21] Appl. No.: 789,597

[22] Filed: Oct. 21, 1985

[30] Foreign Application Priority Data

Oct. 22, 1984 [JP] Japan ................. 59-221853
Dec. 10, 1984 [JP] Japan ................. 59-260453
Dec. 22, 1984 [JP] Japan ................. 59-271303

[51] Int. Cl.$^4$ ............................................. A61K 37/64
[52] U.S. Cl. ........................................ 514/18; 514/19; 514/397; 514/400; 530/331; 548/336; 548/344
[58] Field of Search ............... 548/336, 344; 514/397, 514/400, 18, 19; 530/331

[56] References Cited

U.S. PATENT DOCUMENTS

| | | | |
|---|---|---|---|
| 4,234,571 | 11/1980 | Nestor et al. | 548/344 |
| 4,548,926 | 10/1985 | Matsueda et al. | 548/344 |
| 4,591,648 | 5/1986 | Jones et al. | 548/344 |
| 4,595,677 | 6/1986 | Riniker et al. | 514/17 |
| 4,656,269 | 4/1987 | Iizuka et al. | 544/139 |
| 4,666,888 | 5/1987 | Raddatz et al. | 514/18 |
| 4,698,329 | 5/1987 | Matsueda et al. | 514/18 |
| 4,711,958 | 12/1987 | Iizuka et al. | 544/139 |

FOREIGN PATENT DOCUMENTS

| | | | |
|---|---|---|---|
| 77028 | 4/1983 | European Pat. Off. | 564/152 |
| 77029 | 4/1983 | European Pat. Off. | 564/152 |
| 81783 | 6/1983 | European Pat. Off. | 564/152 |
| 114993 | 8/1984 | European Pat. Off. | 548/344 |
| 173481 | 3/1986 | European Pat. Off. | |
| 58-39149 | 8/1983 | Japan . | |
| 103230 | 12/1984 | Japan | 548/344 |
| 19100 | 8/1985 | Japan | 548/344 |
| 201036 | 4/1986 | Japan | 548/344 |
| 273913 | 7/1986 | Japan | 548/344 |
| 265921 | 12/1986 | Japan | 548/344 |
| 267947 | 12/1986 | Japan | 548/344 |
| 285317 | 12/1986 | Japan | 548/344 |

OTHER PUBLICATIONS

Matsueda et al., "Short Chain Peptide Inhibitors of Human Renin", *Chemistry Letters, Chem. Soc., Japan*, No. 7, pp. 1041–1044 (1985).

Patent Abstracts of Japan, unexamined applications, C Section, vol. 2, No. 43, Mar. 23, 1978, p. 4928, Application No. 51-67001.

Brown et al, "Protection of Histidine Side-Chains, etc.", Chemical Abstracts 95: 220299f (1981).

Colombo et al., "Acid-Labile Histidine Side-Chain Protection," Chemical Abstracts 101: 23914n (1984).

Kobuku et al., "Highly Potent and Specific Inhibitors, etc.," Biochemical and Biophysical Research Comm., vol. 118, No. 3, pp. 929–933 (2–1984).

*Primary Examiner*—Richard A. Schwartz
*Attorney, Agent, or Firm*—Sughrue, Mion, Zinn, Macpeak & Seas

[57] ABSTRACT

Dipeptides are described which are represented by the formula

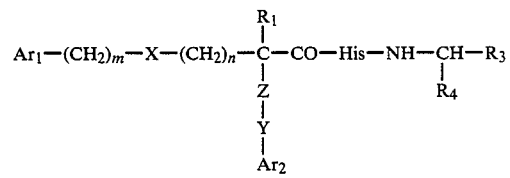

wherein the various substituents are defined hereinbelow.

These compounds have a strong inhibitory efect on human renin, and are useful as a therapeutically active agent for the treatment of hypertension, especially renin-associated hypertension.

16 Claims, No Drawings

DIPEPTIDES AS RENIN INHIBITORS

FIELD OF THE INVENTION

This invention relates to novel peptides useful as a therapeutic agent. More particularly, this invention relates to dipeptides which have a human renin inhibitory effect when administered orally, and thus which are useful for treatment of hypertension, especially renin-associated hypertension.

BACKGROUND OF THE INVENTION

Renin is a proteolytic enzyme having a molecular weight of about 40,000, produced and secreted by juxtaglomerular cells in the kidney. This acts on the plasma renin substrate, angiotensinogen, to yield decapeptide angiotension I which is converted into angiotensin II by angiotensin I converting enzyme.

It is well known that angiotensin II contracts the vascular smooth muscle and acts on the adrenal cortex to screte the aldosterone which regulates salt and water balance. Accordingly, the renin-angiotensin system plays an important role in hypertension. In fact, a specific inhibitor of angiotensin I converting enzyme has been investigated and developed as a practical medicament for hypertension. Thus, an effective inhibitor of renin has long been sought as an agent for treatment of hypertension, especially renin-associated hypertension. As a result, it has been found that certain peptides shown renin inhibitory effect, as described in Biochemical and Biophysical Research Communications, Vol. 118, pages 929–933, 1984; Japanese Patent Publication No. 39149/83, Japanese Patent Applications (OPI) Nos. 110661/84 and 155345/84 (The term "OPI" as used herein refers to a Japanese unexamined published patent application); and European Patent Applicatins 77029(A$_2$), 77028(A$_2$) and 81783(A$_2$).

The noted Biochemical and Biophysical Research Communications article discloses a dipeptide represented by the formula

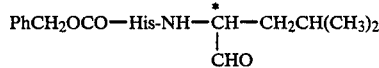

PhCH$_2$OCO—His—NH—$\overset{*}{\text{C}}$H—CH$_2$CH(CH$_3$)$_2$
　　　　　　　　　　　|
　　　　　　　　　　CHO His represents an L-histidyl group, and C* represents an L-configurational carbon atom. However, this peptide shows a weak renin inhibitory activity, and thus was hardly useful as a practical medicament.

Japanese Patent Publication No. 39149/83 above discloses peptides represented by the formula

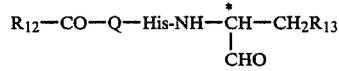

R$_{12}$—CO—Q—His—NH—$\overset{*}{\text{C}}$H—CH$_2$R$_{13}$
　　　　　　　　　　|
　　　　　　　　　CHO wherein R$_{12}$ represents a methyl group, an ethyl group, a benzyl group, an adamantyl group or a benzyloxy group, Q represents an L-phenylalanyl group, an L-prolyl-L-phenylalanyl group or an L-histidyl-L-prolyl-L-phenylalanyl group, His represents an L-histidyl group, R$_{13}$ represents an isopropyl group, and C* represents an L-configurational carbon atom. These peptides show a renin inhibitory effect, however, they are easily digested by proteolytic enzymes of the gastrointestinal tract such as chymotrypsins. Therefore, they have a drawback that their renin inhibitory effect can not be expected when they are administered orally.

On the other hand, the peptides disclosed in the above European Patent Applications are polypeptides and have difficulties in their preparation and purification. Furthermore, they lose their pharmacological effects when administered orally similar to the peptides disclosed in the Japanese Patent Publication No. 39149/83, and the extent to which they are useful is thus limited.

Thus, development of renin inhibitors which can display a sufficient therapeutic effect by oral administration has long been desired.

SUMMARY OF THE INVENTION

Accordingly, an object of this invention is to provide compounds possessing a pharmacological effect.

Another object of this invention is to provide new peptides which exhibit a specific renin inhibitory effect when administered orally to mammalia including humans.

Still another object of this invention is to provide new dipeptides and pharmaceutically acceptable salts thereof.

Yet another object of this invention is to provide pharmaceutical compositions comprising dipeptides or pharamceutically acceptable salts thereof.

A further object of this invention is to provide methods for the treatment of hypertension using dipeptides or pharmaceutically acceptable salts thereof.

Other objects, features and advantages of this invention will become apparent from the following description of the invention.

The present invention provides dipeptides represented by formula (I)

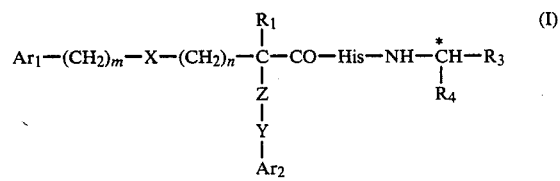

wherein His represents an L-histidyl group, Ar$_1$ represents a phenyl group, a nphthyl group or an indolyl group, Ar$_2$ represents a phenyl group or a naphthyl group, X represents a chemical bond, —NHCO—, —CONH—, —CO—, —CH$_2$—, —NH—, —O— or —(CH=CH)$_p$—, wherein p is 1 or 2, Z represents an oxygen atom or

$\overset{\text{R}_2}{\underset{\text{—CH—}}{|}}$ in which R$_2$ represents a hydrogen atom or may be combined with R$_1$ to form a chemical bond, m and n, which may be the same or different, each represents an integer of from 0 to 3, provided that when X is a chemical bond, the sum of n plus m is from 1 to 6, and when X is not a chemical bond, the sum of n plus m is from 1 to 4, Y represents a chemical bond when X is not a chemical bond, or, when X is a chemical bond, an alkylene group having 1 to 3 carbon atoms, R$_1$ represents a hydrogen atom or combines with R$_2$ to form a chemical bond, R$_3$ represents a formyl group or a hydroxymethyl group, R$_4$ represents an isobutyl group or a benzyl group, and C* represents an L-configurational carbon atom; or a pharmaceutically acceptable salt thereof.

DETAILED DESCRIPTION OF THE INVENTION

These peptides of formula (I) of the present invention can inhibit renin activity in a human renin-sheep renin substrate system. Furthermore, the peptides of the present invention are stable against proteolytic enzymes such as pepsin and chymotrypsins.

These findings demonstrate that the dipeptides of the formula (I) of the present invention exhibit a human renin inhibitory effect when administered orally to mammalia, including humans, and thus are useful for treatment of hypertension, especially renin-associated hypertension.

The dipeptides of formula (I) of the present invention can be prepared by reacting a reactive functional derivative of an acid compound of formula (II)

$$Ar_1-(CH_2)_m-X-(CH_2)_n-\overset{\overset{R_1}{|}}{\underset{\underset{\underset{Ar_2}{|}}{\underset{Y}{|}}{Z}}{C}}-COOH \quad (II)$$

wherein $Ar_1$, $Ar_2$, Y, X, Z, m, n and $R_1$ have the same meanings as defined above, with a compound of formula (III)

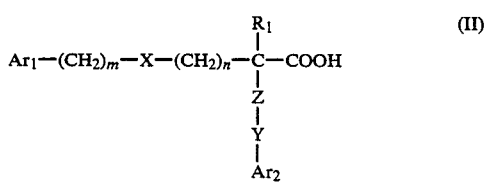

wherein $R_3$, $R_4$ and C* have the same meanings as defined above. Alternatively, dipeptides of formula (I) can be prepared by reacting a compound of formula (IV)

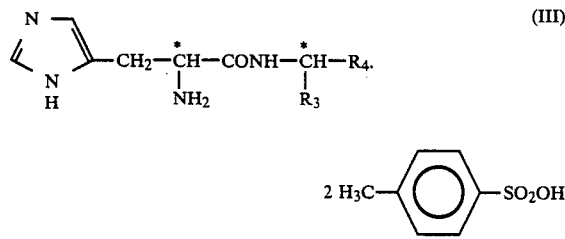

wherein $Ar_1$, $Ar_2$, X, Y, Z, m, n, $R_1$ and C* have the same meanings as defined above, with an acid salt of a compound of formula (V)

$$H_2N-\overset{*}{\underset{\underset{R_3}{|}}{CH}}-R_4 \quad (V)$$

wherein $R_3$, $R_4$ and C* have the same meanings as defined above.

In these processes, the formyl group in the general formulea (III) and (V) are protected with a suitable protective group prior to the reaction of a reactive functional derivative of an acid compound of formula (II) with a compound of formula (III) or the reaction of a compound of formula (IV) with a compound of formula (V), and then after the reaction, said protective group is removed by conventional methods. As examples of the protective group, a group derived from a semicarbazide or an hydroxylamine can be employed, and a group derived from semicarbazide is preferred.

The acid compounds of formula (II), some of which are known, can be prepared by a known method or an analogous method thereof. Examples of the acid compounds include 2-benzyl-3-phenylpropionic acid, 4-phenyl-2-(2-phenethyl)butyric acid, 2-benzyl-5-phenylpentanoic acid, 2-benzyl-7-phenylheptanoic acid, 2-(1-naphthylmethyl)-6-phenylhexanoic acid, 2-benzyl-6-(2-naphthyl)-hexanoic acid, 2-(1-naphthylmethyl)-8-phenyloctanoic acid, 2-(1-naphthylmethylcarbamoyl)-3-phenylpropionic acid, 2-benzyl-3-(1-naphthylmethylcarbamoyl)propionic acid, 3-(benzylcarbamoyl)-2-(1-naphthylmethylene)propionic acid, 2-benzylidene-3-(1-naphthylmethylcarbamoyl)propionic acid, 3-benzylcarbamoyl-2-(1-naphthylmethylene)propionic acid, 2-(1-naphthylmethylene)-3-(phenethylcarbamoyl)propionic acid, 2-benzyl-3-(1-naphthylacetamido)propionic acid, 2-(1-naphthylmethylene)-3-(phenethylcarbamoyl)propionic acid, 2-(1-napthylmethyl)-3-(phenethylcarbamoyl)propionic acid, 2-(1-naphthylmethyl)-3-(phenylcarbamoyl)propionic acid, 3-(benzylcarbamoyl)-2-(1-naphthylmethyl)propionic acid, 3-[2-(3-indolyl)ethylcarbamoyl]-2-(1-naphthylmethyl)propionic acid, 2-(1-naphthylmethyl)-5-phenyl-4-pentenoic acid, 2-(1-naphthylmethyl)-7-phenyl-4,6-heptadienoic acid, 2-(1-naphthylmethyl)-4-phenethoxybutyric acid, 2-(1-naphthylmethyl)-5-phenoxyvaleric acid, 2-(1-naphthylmethyl)-5-phenylvaleric acid, 2-(1-naphthylmethyl)-6-phenylhexanoic acid, 2-(1-naphthoxy)-6-phenylhexanoic acid, 3-[N-carbobenzoxy-N-(3-phenylpropyl)amino]-2-(1-naphthylmethyl)propionic acid, 5-benzoyl-2-(1-naphthylmethyl)valeric acid and the like. These acid compounds have optical isomers and geometrical isomers when they have a double bond, and all isomers may be employed in the present invention.

The compounds of formula (III) can be prepared by reacting L-leucinol or L-leucinal wherein the carbonyl group is protected, with L-histidine wherein the amino group is protected, according to a well known technique of peptide synthesis.

The compounds of formula (IV) can be also prepared by reacting a reactive functional derivative of the acid compound of formula (II) above with L-histidne methyl ester dihydrochloride in N,N-dimethylformamide to obtain a compound of formula (VI)

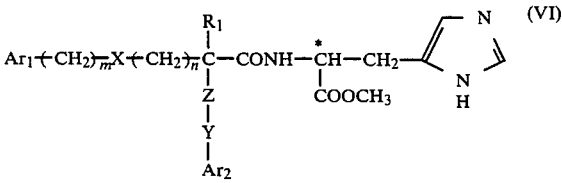

wherein $Ar_1$, $Ar_2$, $R_1$, X, Z, Y, m, n and C* have the same meanings as defined above, and then reacting the resulting product with hydrazine monohydrate in methanol.

The compound of formula (V) can be easily prepared from L-leucine, and as the acid salt, acetic acid salt, p-toluenesulfonic acid salt and the like can be employed.

The reaction of a reactive functional derivative of an acid compound of formula (II) with a compound of formula (III) are well known in the art, and can be carried out according to the procedures described in the literature.

That is, the dipeptides of formula (I) of this invention can be prepared by dissolving an acid compound of the general formula (II) in an inert organic solvent, e.g., chloroform, dichloromethane, N,N-dimethylformamide, acetonitrile and the like, adding 1,1'-carbonyldiimidazole, N,N'-disuccinimidylcarbonate or diphenylphosphoryl azide, reacting the mixture for from about 0.5 to about 3 hours under cooling or at room temperature, adding a compound of formula (III) in an equimolar amount to the acid compound of formula (II) to the reaction mixture, reacting the mixture for from about 1 to about 20 hours at from about 0° C. to about 50° C., and then treating the compound obtained with an aldehyde compound such as formaldehyde, acetaldehyde in the presence of an organic acid, such as acetic acid, chloroacetic acid and the like, or a minimal acid such as hydrochloric acid and the like in methanol to remove the protective group from the carbonyl group.

Also, the amidation described in the reaction of a compound of formula (IV) with a compound of formula (V) can also be carried out by suspending a compound of formula (IV) in N,N-dimethylformamide, adding successively hydrogen chloride in a proportion of from about 3 to about 5 molar amounts per mole of the compound of formula (IV) and isoamyl nitrite in a proportion of from about 1 to about 3 moles per mole of the compound of formula (IV) to the suspension, reacting the mixture for from about 5 minutes to about 30 minutes at from about −20° C. to about −5° C., adjusting a pH of the reaction mixture to about 9 or 9 by an addition of triethylamine, adding the mixture to a solution of a compound of formula (V) in an equimolar amount to the compound of formula (IV) in N,N-dimethylformamide under cooling, preferably at from −20° C. to 0° C., reacting the mixture for from about 5 hours to about 20 hours at from about 0° C. to room temperature, and then treating the reaction mixture according to usual method to obtain the desired product.

Examples of the dipeptides of formula (I) of the present invention include N-(2-benzyl-3-phenylpropionyl)-L-histidyl-L-leucinal, N-[4-phenyl-2-(2-phenethyl)-butanoyl]-L-histidyl-L-lecuinal, N-[2-(1-naphthylmethyl)-6-phenylhexanoyl]-L-histidyl-L-leucinal, N-[2-benzyl-6-(2-naphthyl)hexanoyl]-L-histidyl-L-leucinal, N-[2-(1-naphthylmethyl)-8-phenyloctanoyl]-L-histidyl-L-leucinal, N-(2-benzyl-7-phenylheptanoyl)-L-histidyl-L-leucinal, N-(2-benzyl-5-phenylpentanoyl)-L-histidyl-L-leucinal, N-[(+)-2-(1-naphthylmethyl)-6-phenylhexanoyl]-L-histidyl-L-leucinal, N-[(−)-2-(1-naphthylmethyl)-6-phenylhexanoyl]-L-histidyl-L-leucinal, N-[(±)-2-(1-naphthylmethylcarbamoyl)-3-phenylpropionyl]-L-histidyl-L-leucinal, N-[(±)-2-benzyl-3-(1-naphthylacetamido)propionyl]-L-histidyl-L-leucinal, N-[2-benzylidene-3-(1-naphthylmethylcarbamoyl)propionyl]-L-histidyl-L-leucinal, N-[(±)-2-benzyl-3-(1-naphthylmethylcarbamoyl)propionyl]-L-histidyl-L-leucinal, N-[2-(1-naphthylmethyl)-3-(phenethylcarbamoyl)propionyl]-L-histidyl-L-leucinal, N-[3-(benzylcarbamoyl)-2-(1-naphthylmethyl)propionyl]-L-histidyl-L-leucinal, N-{3-[2-(3-indolyl)ethylcarbamoyl]-2-(1-naphthylmethyl)propionyl}-L-histidyl-L-leucinal, N-[(±)-2-(1-naphthylmethyl-5-phenyl-4-pentenoyl]-L-histidyl-L-leucinal, N-[(±)-2-(1-naphthylmethyl)-7-phenyl-4,6-heptadienoyl]-L-histidyl-L-leucinal, N-[(±)-2-(1-naphthylmethyl)-4-phenethoxybutyryl]-L-histidyl-L-leucinal, N-[(±)-5-benzoyl-2-(1-naphthylmethyl)-valeryl]-L-histidyl-L-leucinal, N-[(±)-2-(1-naphthylmethyl)-5-phenoxyvaleryl]-L-histidyl-L-leucinal, N-[2-(1-naphthylmethyl)-3-(phenethycarbamoyl)propionyl]-L-histidyl-L-leucinol, N-[3-(benzylcarbamoyl)-2-(1-naphthylmethyl)propionyl]-L-histidyl-L-leucinol, N-[2-(1-naphthylmethyl)-3-(phenylcarbamoyl)propionyl]-L-histidyl-L-leucinol, N-{3-[2-(3-indolyl)ethylcarbamoyl]-2-(1-naphthylmethyl)propionyl}-L-histidyl-L-leucinol, N-[(±)-2-(1-naphthylmethyl)-5-phenoxyvaleryl]-L-histidyl-L-leucinol, N-[(±)-2-(1-naphthylmethyl)-4-phenethoxybutyryl)]-L-histidyl-L-leucinol, N-[(+)-2-(1-naphthylmethyl)-6-phenylhexanoyl]-L-histidyl-L-leucinol, N-[(±)-2-(1-naphthylmethyl)-5-phenylvaleryl]-L-histidyl-L-leucinol, N-[(±)-2-(1-naphthoxy)-6-phenylhexanoyl]-L-histidyl-L-leucinol, N-[(±)-5-benzoyl-2-(1-naphthylmethyl)valeryl]-L-histidyl-L-leucinol, N-[(±)-2-(1-naphthylmethyl)-5-phenyl-4-pentenoyl]-L-histidyl-L-leucinol, N-[(±)-2-(1-naphthylmethyl)-7-phenyl-4,6-heptadienoyl]-L-histidyl-L-leucinol, N-[2-(1-naphthylmethylene)-3-(phenethylcarbamoyl)propionyl]-L-histidyl-L-leucinol, N-[2-(1-napthylmethyl)-3-(3-phenylpropylamino)propionoyl]-L-histidyl-L-leucinol and N-[2-(1-naphthylmethyl)-3-(phenethylcarbamoyl)propionyl-L-histidyl-L-alaninol.

More preferred examples of the dipeptide of the present invention include N-[2-(1-naphthylmethyl)-6-phenylhexanoyl]-L-histidyl-L-leucinal, N-[2-(1-naphthylmethyl)-8-phenyloctanoyl]-L-histidyl-L-lecinal, N-[(+)-2-(1-naphthylmethyl)-6-phenylhexanoyl]-L-histidyl-L-leucinal, N-[(−)-2-(1-napthylmethyl)-6-phenylhexanoyl]-L-histidyl-L-leucinal, N-[2-(1-naphthylmethyl)-3-(phenethycarbamoyl)propionyl]-L-histidyl-L-leucinal, N-[3-(benzylocarbmoyl)-2-(1-naphthylmethyl)propionyl]-L-histidyl-L-leucinal, N-{3-[2-(3-indolyl)ethylcarbamoyl]-2-(1-naphthylmethyl)propionyl}-L-histidyl-L-leucinal, N-[(±)-2-(1-naphthylmethyl-5-phenyl-4-pentenoyl]-L-histidyl-L-leucinal, N-[(±)-2-(1-naphthylmethyl)-7-phenyl-4,6-heptadienoyl]-L-histidyl-L-leucinal, N-[(±)-2-(1-naphthylmethyl)-4-phenethoxybutyryl]-L-histidyl-L-leucinal, N-[(±)-5-benzoyl-2-(1-naphthylmethyl)valeryl]-L-histidyl-L-leucinal and N-[(±)-2-(1-naphthylmethyl)-5-phenoxyvaleryl]-L-histidyl-L-leucinal.

Most preferred examples of the dipeptide of the present invention include N-[(+)-2-(1-naphthylmethyl)-6-phenylhexanoyl]-L-histidyl-L-leucinal, N-[2-(1-naphthylmethyl)-3-(phenethylcarbamoyl)propionyl]-L-histidyl-L-leucinal, N-[3-(benzylcarbamoyl)-2-(1-naphthylmethyl)propionyl]-L-histidyl-L-leucinal and N-[(±)-2-(1-naphthylmethyl)-4-phenethoxybutyryl]-L-histidyl-L-leucinal.

The dipetides of formula (I) of the present invention can be converted according to conventional methods to a pharmaceutically acceptable salt thereof. Examples of such pharmaceutically acceptable salts include a hydrochloric acid salt, a sulfuric acid salt, a p-toluenesulfonic acid salt, an acetic acid salt, a citric acid salt, a tartaric acid salt, a succinic acid salt and the like. These salts have a renin inhibitory effect as high as the corresponding compounds having a free amino group and are stable against proteolytic enzymes, and thus they show the desired renin inhibitory effect even upon oral administration.

The peptides for formula (I) of the present invention possess a strong inhibitory effect on human renin and are useful as a therapeuticalldy active agent for treatment of hypertension, especially renin-associated hypertension.

The peptides of formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The dipeptides and the pharmaceuticalldy acceptable salts of the general formula (I) of the present invention can be administered in various dosage forms depending upon the intended therapy. Typical dosage forms which can be used are tablets, pills, powders, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated and made into sugar-coated tablets, gelatin-coated tablets, film-coated tablets, or tablets coated with two or more layers.

When the pharmaceutical composition is formulated into an injectable preparation, it is preferred that the resulting injectable solution and suspension are sterilized and rendered isotonic with respect to blood. In making the pharmaceutical composition into a solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents.

The dosage of the dipeptides of the present invention may be in the range of from about 5 mg to 5,000 mg per body by oral administration, or from about 1 mg to 1,000 mg per body by parenteral administration per day in multiple doses depends upon the type of disease, the severity of condition to be treated, and the like.

This invention is further illustrated in more detail by way of the following examples and reference examples. The melting point of the product obtained was uncorrected. The NMR spectra of the products were measured by JEOL's High Resolution NMR Spectrometer Type JNM-GX 270. The Mass spectra of the products were measured by JEOL's Mass Spectrometer Type JMN-DX 300 according to the FAB method. Thin layer chromatography was carried out using Merck's precoated plates silica gel 60 $F_{254}$ and column chromatography was carried out by employing Merck's Kiesel gel 60 (230–400 mesh). Thin layer chromatography was carried out by using a lower layer of a mixture of chloroform, methanol and water in a proportion of 8/3/1 (by volume) (mixture A) and a mixture of chloroform and methanol in a proportion of 5/1 (by volume) (mixture B) as an eluent, and an $Rf_1$ (mixture A) value and $Rf_2$ (mixture B) value were calculated.

REFERENCE EXAMPLE 1

2-(1-Naphthylmethyl)-6-phenylhexanoic acid

To a solution of 2.62 g of 2-(1-naphthylmethyl)malonic acid diethyl ester in 40 ml of dry 1,2-dimethoxyethane was added 0.46 g of a 50% sodium hydride (suspension in oil) while ice-cooling, and then 2.05 g of 4-phenylbutyl bromide was added dropwise to the mixture. The mixture was heated under reflux for 19 hours. After cooling, an aqueous ether was added to the reaction mixture and the mixture was extracted with diethyl ether. The ethereal layer was washed with a saturated sodium chloride aqueous solution, dried over anhydrous magnesium sulfate, concentrated under reduced pressure. The residue was purified by silica gel flash column chromatography (eluent: benzene/hexane=1/1 by volume) to obtain 2.77 g of 2-(1-naphthylmethyl)-2-(4-phenylbutyl)malonic acid diethyl ester as a colorless oil.

To a solution of 2.76 g of 2-(1-naphthylmethyl)-2-(4-phenylbutyl)malonic acid diethyl ester in 20 ml of dimethyl sulfoxide and 0.5 ml of water was added 1.27 g of lithium chloride, and then the mixture was heated for 8 hours at from 180° to 190° C. After cooling, to the reaction mixture was added water, and the mixture was extracted with ethyl acetate. The organic layer was washed with a saturated sodium chloride aqueous solution, dried over anhydrous magnesium sulfate, and concentrated under reduced pressure to obtain 2.06 g of 2-(1-naphthylmethyl)-6-phenylhexanoic acid ethyl ester as a light brown oil.

To a solution of 2.05 g of 2-(1-naphthylmethyl)-6-phenylhexanoic acid ethyl ester in 30 ml of ethanol was added 10 ml of a 2N-aqueous sodium hydroxide solution. The mixture was heated under reflux for 1.5 hours. The reaction mixture was concentrated under reduced pressure, and to the residue was added water, and the mixture was washed with diethyl ether to remove neutral materials. Then, the aqueous layer was acidified by adding concentrated hydrochloric acid. The solution was extracted with diethyl ether, and the ethereal layer was washed with a saturated sodium chloride aqueous solution, dried over anhydrous magnesium sulfate, and concentrated under reduced pressure to obtain 1.85 g of 2-(1-naphthylmethyl)-6-phenylhexanoic acid as a colorless oil.

IR (neat): $\nu co$ 1690 $cm^{-1}$.

NMR (CDCl$_3$) δ: 1.25–1.9(m, 6H), 2.56(t, 2H), 2.8–3.0(m, 1H), 3.17(dd, 1H, J=7.2, 14.3 Hz), 3.48(dd, 1H, J=7.7, 14.3 Hz), 7.05–8.1(m, 12H).

REFERENCE EXAMPLE 2

The following compounds were prepared in an analogous manner to that described in Reference example 1.

2-Benzyl-6-(2-naphthyl)hexanoic acid

Colorless crystals.

Melting point: 86°–88° C.

IR (KBr): $\nu co$ 1685 $cm^{-1}$

NMR (CDCl$_3$) δ: 1.3–1.8(m, 6H), 2.6–2.85(m, 4H), 2.9–3.05(m, 1H), 7.1–7.85(m, 12H).

2-(1-Naphthylmethyl)-8-phenyloctanoic acid

Colorless viscous oil.
IR (neat): νco 1700 cm$^{-1}$.
NMR (CDCl$_3$) δ: 1.1–1.9(m, 10H), 1.56(t, 2H, J=7.1 Hz), 2.8–2.95(m, 1H), 3.19(dd, 1H, J=8.1, 14.3 Hz), 3.46(dd, 1H, J=7.7, 14.3 Hz), 7.1–8.05(m, 12H).

2-Benzyl-7-phenylheptanoic acid

Colorless viscous oil.
IR (neat): νco 1700 cm$^{-1}$.
NMR (CDCl$_3$) δ: 1.2–1.8(m, 8H), 2.57(t, 2H, J=7.1 Hz), 2.6–2.8(m, 2H), 2.96(dd, 1H, J=7.7, 13.2 Hz), 7.1–7.3(m, 10H).

2-Benzyl-5-phenylpentanoic acid

Colorless viscous oil.
IR (neat): νco 1700 cm$^{-1}$.
NMR (CDCl$_3$) δ: 1.6–1.7(m, 4H), 2.55–3.0(m, 5H), 7.1–7.3(m, 10H).

REFERENCE EXAMPLE 3

4-Phenyl-2-(phenethyl)butyric acid

To a solution of 3.2 g of malonic acid diethyl ester in 20 ml of dry 1,2-dimethoxyethane was added 2.4 g of a 50% sodium hydride (suspension in oil) under cooling, and then to the mixture was added 9.25 g of phenethyl bromide. The mixture was heated under reflux for 16 hours. After cooling, an aqueous diethyl ether was added to the reaction mixture, and the mixture was extracted with diethyl ether. The ethereal layer was washed with a saturated sodium chloride aqueous solution, dried over anhydrous magnesium sulfate, and concentrated under reduced pressure to obtain 5.55 g of a light yellow oil. To 5.52 g of the obtained oil were added 17 g of sodium hydroxide, 60 ml of water and 100 ml of isoamyl alcohol, and the mixture was heated under reflux for 16 hours. The reaction mixture was concentrated under reduced pressure, water was added to the residue, and then the mixture was washed with diethyl ether to remove neutral materials. The aqueous layer was acidified by adding concentrated hydrochloric acid, and the solution was extracted with diethyl ether. The ethereal layer was washed with a saturated sodium chloride aqueous solution, dried over anhydrous magnesium sulfate, and concentrated under reduced pressure. The residue was triturated with n-hexane, and the precipitated crystals were collected by filtration to obtain 3.10 g of 2,2-bis(phenethyl)malonic acid as colorless crystals.

Melting point: 168°–172° C.
IR (KBr): νco 1680 cm$^{-1}$.
NMR (d$_6$-DMSO) δ: 1.95–2.2(m, 4H), 2.3–2.6(m, 4H), 7.05–7.45(m, 10H), 12.5–13.3(br, 2H).

2.95 g of 2,2-Bis(2-phenethyl)malonic acid was heated for 1 hour at from 190° C. to 195° C. After cooling, the reaction mixture was purified by silica gel flash column chromatography (eluent; chloroform) to obtain 2.27 g of 4-phenyl-2-(phenethyl)butyric acid as a light yellow oil.

IR (neat): νco 1690 cm$^{-1}$.
NMR (CDCl$_3$)
δ: 1.75–2.15(m, 4H), 2.4–2.55(m, 1H), 2.55–2.8(m, 4H), 7.05–7.4(m, 10H).

REFERENCE EXAMPLE 4

2-Benzyl-3-phenylpropionic acid

To a solution of 3.2 g of malonic acid diethyl ester in 100 ml of absolute ethanol was added 3.0 g of sodium ethoxide, and then the mixture was stirred for 30 minutes at room temperature. To the reaction mixture was added 6.8 g of benzyl bromide, the reaction mixture was stirred for 30 minutes, and then heated under reflux for 4 hours. The reaction mixture was concentrated under reduced pressure, and the residue was acidified by adding diluted hydrochloric acid. The mixture was extracted with ethyl acetate, and the organic layer was washed successively with a 5% aqueous sodium bicarbonate solution and a saturated sodium chloride aqueous solution, dried over anhydrous magnesium sulfate, and concentrated under reduced pressure. The residue was purified by silica gel flash column chromatography (eluent: dichloromethane) to obtain 6.0 g of dibenzylmalonic acid diethyl ester as a colorless oil. To a solution of 6.0 g of dibenzylmalonic acid diethyl ester obtained in 40 ml of dimethyl sulfoxide and 1.2 ml of water was added 3.7 g of lithium chloride, and then the mixture was heated for 6 hours at from 180° to 190° C. After cooling, water was added to the reaction mixture, and the mixture was extracted with ethyl acetate. The organic layer was washed with a saturated sodium chloride aqueous solution, dried over anhydrous magnesium sulfate, and concentrated under reduced pressure. The residue was purified by silica gel flash column chromatography (eluent: dichloromethane) to obtain 4.2 g of 2-benzyl-3-phenylpropionic acid ethyl ester as a light brown oil.

To a solution of 3.4 g of 2-benzyl-3-phenylpropionic acid ethyl ester in 170 ml of ethanol was added 34 ml of a 2N-aqueous sodium hydroxide solution, and the mixture was heated under reflux for 1.5 hours. The reaction mixture was concentrated under reduced pressure, and water was added to the residue. The mixture was washed with diethyl ether to remove neutral materials, then the aqueous solution was acidified by adding concentrated hydrochloric acid. The aqueous solution was extracted with diethyl ether. The ethereal layer was washed with a saturated sodium chloride aqueous solution, dried over anhydrous magnesium sulfate, and concentrated under reduced pressure to obtain 2.8 g of 2-benzyl-3-phenylpropionic acid as colorless crystals.

Melting point: 87°–89° C.
IR (KBr): νco 1700 cm$^{-1}$.
NMR (CDCl$_3$) δ: 2.7–2.85(m, 2H), 2.9–3.05(m, 3H), 7.1–7.3(m, 10).

REFERENCE EXAMPLE 5

(±)-2-(1-Naphthylmethylcarbamoyl)-3-phenylpropionic acid

A solution of 2.55 g of benzaldehyde, 2.46 g of ethyl cyanoacetate, 0.3 ml of acetic acid and 0.3 ml of piperidine in 20 ml of dry benzene was heated under reflux for 16 hours while removing water formed during the reaction by using a molecular sieve. The reaction mixture was concentrated under reduced pressure, the residue was dissolved in ethyl acetate, and the organic layer was washed with a saturated sodium chloride aqueous solution, dried over anhydrous magnesium sulfate, and concentrated under reduced pressure to obtain 4.57 g of 2-cyano-3-phenylpropenoic acid ethyl ester as colorless crystals.

A solution of 4.56 g of the ester obtained in 30 ml of benzene was hydrogenated over 0.45 g of a 10% palladium/charcoal under a hydrogen atmosphere at room temperature for 4 hours. After filtration of the catalyst, the reaction mixture was concentrated under reduced pressure to obtain 4.26 g of 2-cyano-3-phenylpropionic acid ethyl ester as a colorless oil.

To a solution of 406 mg of 2-cyano-3-phenylpropionic acid ethyl ester in 10 ml of ethanol were added 1.1 ml of a 2N-aqueous sodium hydroxide solution, and then the mixture was stirred for 16 hours at room temperature. The reaction mixture was concentrated under reduced pressure, and the residue was dissolved in water and washed with diethyl ether. The aqueous solution was adjusted to a pH of 2 by adding a 2N-hydrochloric acid and extracted with diethyl ether. The ethereal layer was washed with water, dried over anhydrous magnesium sulfate, and concentrated under reduced pressure to obtain 324 mg of 2-cyano-3-phenylpropionic acid.

To a solution of 88 mg of the acid compound obtained in 5 ml of dry chloroform were added 81 mg of 1,1'-carbonyldiimidazole and 0.22 ml of allyl bromide. The mixture was stirred for 2 hours at room temperature, and then concentrated under reduced pressure. To the residue was added 5 ml of a solution of 79 mg of 1-naphthylmethylamine in 5 ml of dry chloroform, and the mixture was heated for 3 hours at 50° C. The mixture was concentrated under reduced pressure and the residue was dissolved in ethyl acetate. The organic layer eas washed successively with diluted hydrochloric acid, a 5% aqueous sodium bicarbonate solution and a saturated sodium chloride aqueous solution, and then dried over anhydrous magnesium sulfate. The solution was concentrated under reduced pressure to obtain 124 mg of N-(1-naphthylmethyl)-2-cyano-3-phenylpropionamide.

In a mixture of 1 ml of ethanol and 2 ml of water were dissolved 123 mg of the amide obtained and 0.66 g of sodium hydroxide, and the solution was heated under reflux for 16 hours. After removal of ethanol, the residue was washed with diethyl ether, and then adjusted to a pH of 2 by adding a 2N-hydrochloric acid. The solution was extracted with ethyl acetate. The organic layer was washed with water, dried over anhydrous magnesium sulfate, and concentrated under reduced pressure to obtain 103 mg of ($\pm$)-2-(1-naphthylmethylcarbamoyl)-3-phenylpropionic acid as colorless crystals.

Melting point: 142°–145° C.
IR (KBr): $\nu$co 1720, 1620 cm$^{-1}$.
NMR (CDCl$_3$)
$\delta$: 3.0–3.6(m, 3H), 4.76(dd, 1H, J=5.5, 14.0 Hz), 4.80(dd, 1H, J=5.5, 14.0 Hz), 5.8(br, 1H), 7.0–8.0(m, 12H).

REFERENCE EXAMPLE 6

($\pm$)-2-Benzyl-3-(1-naphthylacetamido)propionic acid

A solution of 1.01 g of 2-cyano-3-phenylpropenoic acid ethyl ester and 0.7 ml of concentrated hydrochloric acid in 20 ml of ethanol was hydrogenated over 0.1 g of platinum oxide under a hydrogen atmosphere at room temperature for 5 hours. After filtration of the catalyst, the filtrate was concentrated under reduced pressure. The residue was dissolved in water, washed with benzene, and then made alkaline by adding a 5% aqueous sodium bicarbonate solution. The alkaline solution was extracted with diethyl ether, the ethereal layer was washed with water and dried over anhydrous magnesium sulfate. Hydrogen chloride gas was passed into the ethereal solution. The ethereal solution was concentrated under reduced pressure to obtain 832 mg of 3-amino-2-benzylpropionic acid ethyl ester hydrochloride as colorless crystals.

A solution of 173 mg of 1-naphthylacetic acid and 151 mg of 1,1'-carbonyldiimidazole in dry dichloromethane was stirred for 1 hour at room temperature. To the mixture was added 227 mg of 3-amino-2-benzylpropionic acid ethyl ester obtained, and the mixture was heated under reflux for 16 hours. The reaction mixture was concentrated under reduced pressure, and the residue was dissolved in ethyl acetate, and then the organic layer was washed successively with a 1N-hydrochloric acid, a 5% aqueous sodium bicarbonate solution and water. The organic layer was dried over anhydrous magnesium sulfate and concentrated under reduced pressure. The residue was purified by preparative silica gel thin layer chromatography (developing solvent: chloroform/ethanol=5/1 by volume) to obtain 169 mg of 2-benzyl-3-(1-naphthylacetamido)propionic acid ethyl ester as colorless crystals.

A mixture of 168 mg of the propionic acid ethyl ester obtained, 0.5 ml of a 1N-aqueous sodium hydroxide solution and 5 ml of ethanol was stirred for 4 hours at room temperature. The mixture was concentrated under reduced pressure, and the residue was dissolved in water, washed with ether, and adjusted to a pH of 2 by the addition of a 1N-hydrochloric acid. The acidic solution was extracted with ethyl acetate. The organic layer was washed with water, dried over anhydrous magnesium sulfate, and concentrated under reduced pressure to obtain 140 mg of ($\pm$)-2-benzyl-3-(1-naphthylacetamido)propionic acid as colorless crystals.

Melting point: 156°–160° C.
IR (KBr): $\nu$co 1700, 1620 cm$^{-1}$.
NMR (CDCl$_3$) $\delta$: 2.5–2.9(m, 3H), 3.1–3.5(m, 2H), 4.00(s, 2H), 5.7(br, 1H), 6.9–8.0(m, 12H).

REFERENCE EXAMPLE 7

2-(1-Naphthylmethylene)-3-phenethylcarbamoyl)propionic acid

To a solution of 8.71 g of succinic acid ethyl ester and 7.81 g of 1-naphthylaldehyde in 50 ml of absolute ethanol was added 3.02 g of a 50% sodium hydride (suspension in oil) under ice-cooling, and then the mixture was heated under reflux for 3 hours. After cooling, the reaction mixture was concentrated under reduced pressure. Water was added to the residue, and the mixture was extracted with diethyl ether to remove neutral materials. The aqueous layer was acidified by adding concentrated hydrochloric acid and extracted with diethyl ether. The ethereal layer was washed with a saturated sodium chloride aqueous solution, and dried over anhydrous magnesium sulfate. The ethereal solution was concentrated under reduced pressure to obtain 11.8 g of 3-ethoxycarbonyl-4-(1-naphthyl-3-butenoic acid as a yellow oil.

A mixture of 11.75 g of the butenoic acid obtained, 100 ml of a 1N-aqueous sodium hydroxide solution and 85 ml of ethanol was heated for 1.5 hours at 50° C. The reaction mixture was concentrated under reduced pressure, and water was added to the residue. The mixture was washed with diethyl ether to remove neutral materials. The aqueous layer was acidified with concentrated hydrochloric acid and then extracted with diethyl ether. The ethereal layer was washed with a saturated sodium chloride aqueous solution, and then dried over anhydrous magnesium sulfate. The solution ethereal layer was concentrated under reduced pressure to obtain 7.65 g of 2-(1-naphthylmethylene)succinic acid as yellow crystals.

A mixture of 7.6 g of 2-(1-naphthylmethylene)succinic acid obtained and 130 ml of acetic anhydride was heated under reflux for 1 hour. The reaction mixture was concentrated under reduced pressure, and 50 ml of benzene was added to the residue. The precipitated crystals were collected by filtration to obtain 3.4 g of 2-(1-naphthylmethylene)succinic anhydride as orange yellow crystals.

A solution of 1.50 g of the succinic anhydride obtained and 0.76 g of phenethylamine in 30 ml of dichloromethane was stirred for 2 hours at room temperature. The precipitated crystals were collected by filtration to obtain 2.01 g of 2-(1-naphthylmethylene)-3-(phenethylcarbamoyl)propionic acid as colorless crystals.

Melting point: 183°–187° C.
IR (KBr): $\nu$co 1670, 1640 cm$^{-1}$.
NMR (d$_6$-DMSO) δ: 2.69(t, 2H, J=7.1 Hz), 3.15(s, 2H), 3.26(t, 2H, J=7.1 Hz), 7.1–8.1(m, 13H), 8.20(s, 1H).

REFERENCE EXAMPLE 8

The following compounds were prepared in an analogous manner to that described in Reference example 7.

2-Benzylidene-3-(1-naphthylmethylcarbamoyl)propionic acid

White powder.
Melting point: 207°–209° C.
IR (KBr): $\nu$co 1670, 1640 cm$^{-1}$.
NMR (d$_6$-DMSO) δ: 3.37(s, 2H), 4.77(s, 2H), 7.30–7.65(m, 9H), 7.82–8.20(m, 2H).

3-(Benzylcarbamoyl)-2-(1-naphthylmethylene)propionic acid

White powder.
Melting point: 201°–203° C.
IR (KBr): $\nu$co 1675, 1645 cm$^{-1}$.
NMR (d$_6$-DMSO) δ: 3.24(s, 2H), 4.29(d, 2H, J=6.0 Hz), 7.2–8.1(m, 12H), 8.22(s, 1H), 8.35–8.55(br. 1H).

REFERENCE EXAMPLE 9

(±)-2-(1-Naphthylmethyl)-3-(phenethylcarbamoyl)propionic acid

A solution of 500 mg of 2-(1-naphthylmethylene)-3-(phenethylcarbamoyl)propionic acid in 50 ml of acetic acid was hydrogenated over 250 mg of a 10% palladium/charcoal under a hydrogen atmosphere at room temperature. After filtration of the catalyst, the filtrate was concentrated under reduced pressure, and hexane was added to the residue. The precipitates were collected to obtain 500 mg of (±)-2-(1-naphthylmethyl)-3-(phenetylcarbamoyl)propionic acid as colorless crystals.

Melting point: 131°–135° C.
IR (KBr): $\nu$co 1720, 1640 cm$^{-1}$.
NMR (d$_6$-DMSO) δ: 2.15–2.55(m, 2H), 2.68(t, 2H, J=7.1 Hz), 3.0–3.5(m, 5H), 7.1–8.2(m, 13H)

REFERENCE EXAMPLE 10

The following compounds were prepared in an analogous manner to that described in Reference example 9.

(±)-2-Benzyl-3-(1-naphthylmethylcarbamoyl)propionic acid

White powder
Melting point: 148°–151° C.
IR (KBr): $\nu$co 1720, 1620 cm$^{-1}$.
NMR (d$_6$-DMSO) δ: 2.5–3.2(m, 5H), 4.82(d, 2H, J=9 Hz), 7.22–7.45(m, 5H), 7.52–7.70(m, 4H), 7.90–8.22(m, 3H)

(±)-2-(1-Naphthylmethyl)-3-(phenylcarbamoyl)propionic acid

Colorless crystals.
Melting point: 146°–160° C.
IR (KBr): $\nu$co 1700, 1680 cm$^{-1}$.
NMR (d$_6$-DMSO) δ: 2.3–2.8(m, 2H), 3.1–3.5(m, 3H), 6.9–8.35(m, 12H), 10.02(s, 1H), 11.7–12.5(br, 1H)

(±)-3-(Benzylcarbamoyl)-2-(1-naphthylmethyl)propionic acid

White powder.
Melting point: 134°–138° C.
IR (KBr): 84 co 1705, 1640 cm$^{-1}$.
NMR (d$_6$-DMSO) δ: 2.25–2.65(m, 2H), 3.05–3.4(m, 3H), 4.25(d, 2H, J=5.5 Hz), 7.15–8.2(m, 12H), 8.35–8.55(br, 1H).

REFERENCE EXAMPLE 11

(±)-3-[2-(3-Indolyl)ethylcarbamoyl]-2-(1-naphthylmethyl)propionic acid

A solution of 2.0 g of 3-ethoxycarbonyl-4-(1-naphthyl)-3-butenoic acid in 100 ml of acetic acid was hydrogenated over 900 mg of a 10% palladium/charcoal under a hydrogen atmosphere at room temperature. After filtration of the catalyst, the reaction solution was concentrated under reduced pressure to obtain 1.46 g of 3-ethoxycarbonyl-4-(1-naphthyl)butyric acid as a brown oil.

To a solution of 1.45 g of the butyric acid obtained in 30 ml of dichloromethane was added 0.86 g of 1,1′-carbonyldiimidazole. The mixture was stirred for 1 hour at room temperature. Then, 0.82 g of triptamine was added to the reaction mixture, and the mixture was stirred for 1.5 hours. The reaction mixture was concentrated under reduced pressure, and a 5% aqueous sodium bicarbonate solution was added to the residue. The mixture was extracted with ethyl acetate. The organic layer was washed successively with water, diluted hydrochloric acid and water, then dried over anhydrous magnesium sulfate, and concentrated under reduced pressure. The residue was purified by silica gel flash column chromatography (eluent: ethyl acetate/benzene=1/1 by volume) to obtain 1.41 g of 3-[2-(3-indolyl)ethylcarbamoyl]-2-(1-naphthylmethyl)propionic acid ethyl ester as a light brown powder.

A mixture of 1.40 g of the ester compound obtained, 2 ml of a 2N-aqueous sodium hydroxide solution and 10 ml of ethanol was warmed for 10 minutes at 40° C., and the mixture was concentrated under reduced pressure. Water was added to the residue and the mixture was washed with diethyl ether to remove neutral materials. The aqueous layer was acidified by adding concentrated hydrochloric acid and extracted with diethyl ether. The ethereal layer was washed with a saturated sodium chloride aqueous solution, dried over anhydrous magnesium sulfate, and concentrated under reduced pressure to obtain 1.15 g of (±)-3-[2-(3-indolyl)e- thylcarbamoyl]-2-(1-naphthylmethyl)propionic acid as a light brown powder.

Melting point: 73°–75° C.
IR (KBr): νco 1700, 1620 cm$^{-1}$.
NMR (CDCl$_3$) δ: 2.2–3.75(m, 9H), 5.2–5.65(m, 1H), 6.4–8.15(m, 13H).

REFERENCE EXAMPLE 12

(±)-2-(1-Naphthylmethyl)-5-phenyl-4-pentenoic acid

To a solution of 1.50 g of 2-(1-naphthylmethyl)malonic acid diethyl ester in 20 ml of 1,2-dimethoxyethane was added 0.3 g of a 50% sodium hydride (suspension in oil) under cooling, and then the mixture was stirred for 1 hour. To the mixture was added 1.18 g of cinnamyl bromide, and the mixture was heated under reflux for 5 hours. After cooling, water was added to the reaction mixture, and the mixture was extracted with diethyl ether. The ethereal layer was washed with a saturated sodium chloride aqueous solution, and dried over anhydrous magnesium sulfate. The ethereal layer was concentrated under reduced pressure, and the residue was purified by silica gel flash column chromatography (eluent: benzene/hexane=1/1 by volume) to obtain 1.6 g of 2-cinnamyl-2-(1-naphthylmethyl)malonic acid diethyl ester as a colorless oil.

To a solution of 1.5 g of the malonic acid diethyl ester obtained in 10 ml of dimethyl sulfoxide and 0.3 ml of water was added 0.92 g of lithium chloride, and the mixture was heated for 4.5 hours at from 180° to 190° C. After cooling, water was added to the reaction mixture, and the mixture was extracted with diethyl ether. The ethereal layer was washed with a saturated sodium chloride aqueous solution, dried over anhydrous magnesium sulfate, and concentrated under reduced pressure to obtain 0.85 g of 2-(1-naphthylmethyl)-5-phenyl-4-pentenoic acid ethyl ester as a yellow oil.

To a solution of 0.84 g of the ester compound obtained in 20 ml of ethanol was added 3.5 ml of a 2N-aqueous sodium hydroxide solution, and the mixture was heated under reflux for 4 hours. The reaction mixture was concentrated under reduced pressure, and water was added to the residue. The mixture was washed with diethyl ether to remove neutral materials. The aqueous layer was acidified with concentrated hydrochloric acid and extracted with diethyl ether. The ethereal layer was washed with a saturated sodium chloride aqueous solution, dried over anhydrous magnesium sulfate, and concentrated under reduced pressure to obtain 0.37 g of (±)-2-(1-naphthylmethyl)-5-phenyl-4-pentenoic acid as colorless crystals.

Melting point: 135°–137° C.
IR (KBr): νco 1695 cm$^{-1}$.
NMR (d$_6$-DMSO) δ: 2.4–2.6(m, 2H), 2.8–2.95(m, 1H), 3.2–3.4(m, 2H), 6.2–6.35(m, 1H), 6.45(d, 1H, J=15.9 Hz), 7.15–8.15(m, 12H), 12.21(s, 1H).

REFERENCE EXAMPLE 13

The following compounds were prepared in an analogous manner to that described in Reference example 12.

(±)-2-(1-Naphthylmethyl)-7-phenyl-4,6-heptadienoic acid

Yellow amorphous powder
Melting point: 39°–40° C.
IR (KBr): νco 1690 cm$^{-1}$.
NMR (CDCl$_3$) δ: 2.35–2.65(m, 2H), 2.95–3.6(m, 3H), 5.7–5.85(m, 1H), 6.2–6.8(m, 3H), 7.15–8.1(m, 12H).

(±)-2-(1-Naphthylmethyl)-4-phenethoxybutyric acid

Colorless oil.
IR (neat): νco 1715 cm$^{-1}$.
NMR (CDCl$_3$) δ: 1.75–2.1(m, 2H), 2.80(t, 2H, J=7.1 Hz), 2.95–3.1(m, 1H), 3.19(dd, 1H, J=7.7, 13.7 Hz), 3.4–3.6(m, 5H), 7.1–8.1(m, 12H)

(±)-2-(1-Naphthylmethyl)-5-phenoxyvaleric acid

Colorless viscous oil.
IR (neat): νco 1700 cm$^{-1}$
NMR (CDCl$_3$) δ: 1.7–2.05(m, 4H), 2.85–3.05(m, 1H), 3.21(dd, 1H, J=7.1, 14.3 Hz), 3.53(dd, 1H, J=7.1, 14.3 Hz), 3.92(t, 2H, J=5.5 Hz), 6.8–8.1(m, 12H).

(±)-2-(1-Naphthylmethyl)-5-phenylvaleric acid

Colorless oil.
IR (neat): νco 1700 cm$^{-1}$.
NMR (CDCl$_3$) δ: 1.61–1.81(m, 4H), 2.55–2.58(m, 2H), 2.88–2.92(m, 1H), 3.17(dd, 1H, J=3.6, 13.9 Hz), 3.46(dd, 1H, J=3.6, 13.9 Hz), 7.0–7.4(m, 7H), 7.49(q, 2H, J=1.6 Hz), 7.73(d, 1H, J=7.7 Hz), 7.86(d, 1H, J=7.7 Hz), 8.00(d, 1H, J=7.7 Hz).

REFERENCE EXAMPLE 14

(±)-5-Benzoyl-2-(1-naphthylmethyl)valeric acid

To a solution of 2.0 g of 3-benzoylpropionic acid methyl ester in 50 ml of dry benzene were added 0.7 ml of ethylene glycol and 0.01 g of anhydrous-p-toluenesulfonic acid and the mixture was heated under reflux for 17 hours while removing water formed during the reaction by using a molecular sieve. After cooling, the reaction mixture was washed with a saturated sodium chloride aqueous solution, and concentrated under reduced pressure. The residue was purified by silica gel flash column chromatography (eluent: benzene/hexane=1/1 by volume) to obtain 1.8 g of 4,4-ethylenedioxy-4-phenylbutyric acid methyl ester.

To a solution of 1.7 g of the ester compound obtained in 20 ml of dry diethyl ether was added 0.7 g of lithium aluminum hydride under ice-cooling, the mixture was stirred for 1 hour at 0° C., and then heated under reflux for 17 hours. After cooling, the reaction mixture was treated successively with an aqueous diethyl ether solution and water, and the precipitate was filtered off. The filtrate was dried over anhydrous magnesium sulfate, and concentrated under reduced pressure. The residue was purified by silica gel flash column chromatography (eluent: benzene/ethyl acetate=10/1 by volume) to obtain 1.3 g of 4,4-ethylenedioxy-4-phenylbutyl alcohol.

To a solution of 1.2 g of the alcohol compound obtained in 20 ml of acetonitrile were added 1.2 g of 1,1'-carbonyldiimidazole and 2.5 ml of allyl bromide. The mixture was stirred for 2 hours at room temperature and then heated under reflux for 1.5 hours. After cooling, water was added to the reaction mixture, and the mixture was extracted with diethyl ether. The ethereal layer was washed with a saturated sodium chloride aqueous solution, dried over anhydrous magnesium sulfate, and concentrated under reduced pressure to obtain 1.1 g of 4,4-ethylenedioxy-4-phenylbutyl bromide as colorless crystals.

To a solution of 1.1 g of 2-(1-naphthylmethyl)malonic acid diethyl ester in 20 ml of dry 1,2-dimethoxyethane was added 0.22 g of a 50% sodium hydride (suspension in oil) under cooling, the mixture was stirred for 1 hour. To the reaction mixture was added 1.0 g of 4,4-ethylenedioxy-4-phenylbutyl bromide obtained, the mixture was heated under reflux for 17 hours. After cooling, water was added to the reaction mixture, and the mixture was extracted with diethyl ether. The ethereal layer was washed with a saturated sodium chloride aqueous solution, dried over anhydrous magnesium sulfate, and concentrated under reduced pressure. The residue was purified by silica gel flash column chromatography (eluent: benzene/hexane=1/1 by volume) to obtain 1.2 g of 2-(4,4-ethylenedioxy-4-phenylbutyl)-2-(1-naphthylmethyl)malonic acid diethyl ester.

To a solution of 1.15 g of the diethyl ester compound obtained in 5 ml of dimethyl sulfoxide and 0.13 ml of water was added 0.52 g of lithium chloride, and the mixture was heated at from 180° to 190° C. for 2.5 hours. After cooling, water was added to the reaction mixture, and the mixture was extracted with diethyl ether. The ethereal layer was washed with a saturated sodium chloride aqueous solution, dried over anhydrous magnesium sulfate, and concentrated under reduced pressure to obtain 0.84 g of 6,6-ethylenedioxy-2-(1-naphthylmethyl)-6-phenylhexanoic acid ethyl ester as a colorless oil.

To a solution of 0.83 g of the ester compound obtained in 30 ml of acetone was added 6 ml of a 1N-hydrochloric acid, and the mixture was heated under reflux for 3.5 hours. The reaction mixture was concentrated under reduced pressure, and the residue was dissolved in diethyl ether. The ethereal solution was washed successively with a saturated aqueous sodium bicarbonate solution and a saturated aqueous sodium chloride solution, dried over anhydrous magnesium sulfate, and concentrated under reduced pressure to obtain 0.73 g of 5-benzoyl-2-(1-naphthylmethyl)valeric acid ethyl ester as a colorless oil.

To a solution of 0.72 g of the ester compound obtained in 10 ml of ethanol was added 2.5 ml of a 2N-aqueous sodium hydroxide solution, the mixture was heated under reflux for 2 hours. The reaction mixture was concentrated under reduced pressure, and water was added to the residue. The mixture was washed with diethyl ether to remove neutral materials. The aqueous layer was acidified by adding concentrated hydrochloric acid and extracted with diethyl ether. The ethereal layer was washed with a saturated sodium chloride aqueous solution, dried over anhydrous magnesium sulfate, and concentrated under reduced pressure to obtain 0.6 g of ($\pm$)-5-benzoyl-2-(1-naphthylmethyl)valeric acid as colorless crystals.

Melting point: 134°-136° C.
IR (KBr): $\nu$co 1730, 1700 cm$^{-1}$.
NMR (CDCl$_3$) $\delta$: 1.65–1.95(m, 4H), 2.85–3.0(m, 3H), 3.21(dd, 1H, J=7.1, 14.3 Hz), 3.52(dd, 1H, J=7.1, 14.3 Hz), 7.3–8.1(m, 2H).

REFERENCE EXAMPLE 15

($\pm$)-2-(1-Naphthoxy)-6-phenylhexanoic acid

To a mixture of 5 ml of dry tetrahydrofuran and 0.26 g of 50% sodium hydride (suspension in oil) were added 0.7 ml of diisopropylamine and 1.0 g of 1-naphthoxyacetic acid with stirring under an argon atmosphere under ice-cooling. The mixture was heated for 30 minutes at 50° C., and then heated under reflux for 15 minutes. After cooling below 5° C., to the reaction mixture was added dropwise 3.5 ml of n-butyllithium (as a 1.6 mole hexane solution), the mixture was stirred below 10° C. for 20 minutes, and then warmed for 20 minutes at 30° C. After cooling below 5° C. again, 1.00 g of 4-phenylbutyl bromide was added to the reaction mixture. The mixture was stirred for 30 minutes at below 5° C., and then warmed for 1 hour at 30° C. with stirring. After cooling, the reaction mixture was washed with diethyl ether to remove neutral materials. The aqueous layer was acidified by adding concentrated hydrochloric acid, and extracted with ethyl acetate. The organic layer was washed with a saturated sodium chloride aqueous solution, dried over anhydrous magnesium sulfate, and then concentrated under reduced pressure. The residue was purified by silica gel flash column chromatography (eluent: benzene) to obtain 0.37 g of ($\pm$)-2-(1-naphthoxy)-6-phenylhexanoic acid as colorless crystals.

Melting point: 91°-94° C.
IR (KBr): $\nu$co 1700 cm$^{-1}$.
NMR (CDCl$_3$) $\delta$: 1.6–1.8(m, 4H), 2.05–2.2(m, 2H), 2.64(t, 2H, J=7.1 Hz), 4.8–4.9(m, 1H), 6.7–8.3(m, 12H).

REFERENCE EXAMPLE 16

($\pm$)-3-[N-Carbobenzoxy-N-(3-phenylpropyl)amino]-2-(1-naphthylmethyl)propionic acid To a solution of 7.8 g of cyanoacetic acid ethyl ester and 10.0 g of 1-naphthylaldehyde in 150 ml of benzene were added 2 ml of piperidine and 2 ml of acetic acid, the mixture was heated under reflux for 3 hours while removing water formed during the reaction using a molecular sieve. After cooling, the reaction mixture was washed successively with a saturated sodium bicarbonate aqueous solution, water, diluted hydrochloric acid and water, dried over anhydrous magnesium sulfate, and then concentrated under reduced pressure. The residue was recrystallized from benzene-hexane to obtain 13.8 g of 2-cyano-3-(1-naphthyl)propenoic acid ethyl ester as light yellow crystals.

A solution of 13.6 g of the ester compound obtained in 300 ml of benzene was hydrogenated over 1.3 g of a 10% palladium/charcoal under atmospheric pressure. After filtration of the catalyst, the filtrate was concentrated under reduced pressure to obtain 13.6 g of 2-cyano-3-(1-naphthyl)propionic acid ethyl ester as a colorless oil.

A solution of 6.22 g of 2-cyano-3-(1-naphthyl)propionic acid ethyl ester and 50 ml of a 2N-hydrochloric acid in 300 ml of ethanol was hydrogenated over 600 mg of platinum oxide under atmospheric pressure. After filtration of the catalyst, the filtrate was concentrated under reduced pressure, and water was added to the residue. The mixture was washed with diethyl ether to remove neutral materials. The aqueous layer was neutralized by adding sodium bicarbonate, and then extracted with ethyl acetate. The organic layer was washed with a saturated sodium chloride aqueous solution and dried over anhydrous magnesium sulfate. An absolute ethanol solution containing hydrogen chloride was added to the organic layer. The organic layer was concentrated under reduced pressure, and hexane was added to the residue, and the resulting precipitates were collected by filtration to obtain 3.20 g of 3-amino-2-(1-naphthylmethyl)propionic acid ethyl ester hydrochloride as colorless crystals.

To a solution of 1.67 g of the hydrochloride salt obtained and 0.77 g of 3-phenylpropionaldehyde in 20 ml of ethanol was added 0.36 g of sodium cyanoborohydride at room temperature with stirring, and the mixture was stirred for 70 hours. The reaction mixture was acidified by adding concentrated hydrochloric acid, then neutralized with sodium bicarbonate, and extracted with ethyl acetate. The organic layer was washed with a saturated sodium chloride aqueous solution, dried over anhydrous magnesium sulfate, and then concentrated under reduced pressure. The residue was purified by silica gel flash column chromatography (eluent: chloroform/methanol=50/1 by volume) to obtain 1.42 g of 2-(1-naphthylmethyl)-3-(3-phenylpropylamino)propionic acid ethyl ester as a colorless oil.

To a solution of 1.40 g of the ester compound obtained in 20 ml of dioxane and 20 ml of water were successively added dropwise 0.84 g of sodium bicarbonate and 0.68 g of carbobenzoxy chloride under cooling with stirring. The mixture was stirred for 1 hour at room temperature. The reaction mixture was concentrated under reduced pressure, and water was added to the residue. The mixture was extracted with diethyl ether. The ethereal layer was washed with diluted hydrochloric acid and water, dried over anhydrous magnesium sulfate, and concentrated under reduced pressure to obtain 1.75 g of 3-[N-carbobenzoxy-N-(3-phenylpropyl)amino]-2-(1-naphthylmethyl)propionic acid ethyl ester as a colorless oil.

A solution of 1.73 g of the ester compound obtained and 5 ml of a 2N-aqueous sodium hydroxide solution in 100 ml of ethanol was heated at 60° C. for 1 hour. The reaction mixture was concentrated under reduced pressure, and water was added to the residue. The mixture was washed with diethyl ether to remove neutral materials, and the aqueous layer was acidified by adding concentrated hydrochloric acid, and extracted with diethyl ether. The ethereal layer was washed with a saturated sodium chloride aqueous solution, dried over anhydrous magnesium sulfate, and concentrated under reduced pressure to obtain 1.43 g of (±)-3-[N-carbobenzoxy-N-(3-phenylpropyl)amino]-2-(1-naphthylmethyl)-propionic acid as a yellow oil.

IR (neat): $\nu$1690 cm$^{-1}$.

NMR (CDCl$_3$) $\delta$: 1.5–3.7(m, 11H), 4.9–5.2(m, 2H), 6.9–8.0(m, 17H).

REFERENCE EXAMPLE 17

The optical resolution of (±)-2-(1-naphthylmethyl)-6-phenylhexanoic acid

A mixture of 5.0 g of (±)-2-(1-naphthylmethyl)-6-phenylhexanoic acid and 2.27 g of (−)-norephedrine was dissolved in 50 ml of methanol, and the mixture was concentrated under reduced pressure. The residue was dissolved in 60 ml of ethyl acetate with heating to 40° C. and the solution was allowed to stand overnight at room temperature. The precipitate was collected by filtration and recrystallized three times from ethyl acetate to obtain 1.5 g of the norephedrine salt (melting point 128°–131° C.). The resulting salt was dissolved in 30 ml of methanol, and 5 ml of a 1N-hydrochloric acid was added to the solution. The mixture was extracted with diethyl ether, and the ethereal layer was washed with water, dried over anhydrous magnesium sulfate, and concentrated under reduced pressure to obtain 0.95 g of (+)-2-(1-naphtylmethyl)-6-phenylhexanoic acid as a colorless viscous oil.

$[\alpha]_D^{28}$ +2.54 (MeOH).

On the other hand, the filtrate obtained from the first recrystallization was concentrated, and the residue was recrystallized three times in the same manner as described above. The combined filtrate was concentrated under reduced pressure to obtain 2.2 g of a solid substance. The solid was recrystallized from isopropyl ether to obtain 1.1 g of the norephedrine salt (melting point 94°–97° C.). The resulting crystals were dissolved in 15 ml of methanol. The solution was neutralized with 3 ml of a 1N-hydrochloric acid, and the solution was extracted with diethyl ether. The ethereal layer was washed with water, dried over anhydrous magnesium sulfate, and concentrated under reduced pressure to obtain 0.69 g of (−)-2-(1-naphtylmethyl)-6-phenylhexanoic acid as a colorless viscous oil.

$[\alpha]_D^{28}$ −2.50 (MeOH).

REFERENCE EXAMPLE 18

L-Histidyl-L-leucinal semicarbazone.bis(p-toluenesulfonic acid) salt of L-histidyl leucinal semicarbazone To a suspension of 2.0 g of N-benzyloxycarbonyl-L-histidine hydrazide in 25 ml of N,N-dimethylformamide were added 4.3 ml of a dry, 5.1N-hydrogen chloride in N,N-dimethylformamide solution at −20° C. Then 1.1 ml of isoamyl nitrite were added to the mixture, and the mixture was stirred.

After disappearance of the hydrazide compound, the mixture was cooled to −30° C. and neutralized with 3.1 ml of triethylamine to prepare a cold solution of N-benzyloxycarbonyl-L-histidine azide. The cold azide solution was added to a solution of 1.51 g of L-leucinal semicarbazone acetic acid salt and 2.8 ml of triethylamine in 30 ml of N,N-dimethylformamide under ice-cooling, and the solution was stirred overnight while ice-cooling. The reaction mixture was concentrated under reduced pressure, and to the residue was added a 5% aqueous sodium bicarbonate solution. The solution was extracted with ethyl acetate. The organic layer was washed with a saturated sodium chloride aqueous solution, dried over anhydrous magnesium sulfate, and concentrated under reduced pressure. The residue was purified by silica gel flash column chromatography (eluent: chloroform/methanol=10/1 by volume) to obtain 1.81 g as a white powder.

Melting point: 105°–111° C.

Rf$_1$ value: 0.37.

A mixture of 1.0 g of the powder obtained and 0.78 g of anhydrous p-toluenesulfonic acid was dissolved in 25 ml of methanol, and the solution was hydrogenated over 100 mg of a 10% palladium carbon and 300 mg of activated charcoal under a hydrogen atmosphere at room temperature. After filtration of the catalyst and charcoal, the filtrate was concentrated under reduced pressure. The residue was washed with diethyl ether to obtain 1.25 g of bis(p-toluenesulfonic acid) salt of L-histidyl-L-leucinal semicarbazone.

Melting point: 126°–130° C.

NMR (d$_6$-DMSO) $\delta$: 0.88(d, 6H, J=6.0 Hz), 1.25–1.7(m, 3H), 2.30(s, 6H), 3.05–3.3(m, 2H), 4.1–4.3(m, 1H), 4.35–4.55(m, 1H), 6.0–6.4(br, 2H), 7.06(d, 1H, J=3.9 Hz), 7.14(d, 4H, J=7.7 Hz), 7.43(s, 1H), 7.52(d, 4H, J=7.7 Hz), 8.1–8.5(br, 3H), 8.53(d, 1H, J=8.2 Hz), 9.01(s, 1H), 9.96(s, 1H).

REFERENCE EXAMPLE 19

N-[2-(1-Naphthylmethyl)-6-phenylhexanoyl]-L-histidine hydrazide

To a solution of 3.32 g of 2-(1-naphthylmethyl)-6-phenylhexanoic acid in 50 ml of dry acetonitrile were added 2.70 g of N,N′-disuccinimidylcarbonate and 2.0 ml of triethylamine with stirring at room temperature, and the mixture was stirred for 1 hour. The reaction mixture was added dropwise to a mixture of 2.42 g of L-histidine methyl ester dihydrochloride, 6 ml of N-methylmorpholine, 120 ml of dry N,N-dimethylformamide and 300 ml of dry chloroform, and the resulting mixture was stirred for 24 hours at 50° C. The reaction mixture was concentrated under reduced pressure and a 5% aqueous sodium bicarbonate solution was added to the residue and the mixture was extracted with ethyl acetate. The organic layer was washed with a saturated sodium chloride aqueous solution, dried over anhydrous magnesium sulfate, and concentrated under reduced pressure. The residue was purified by silica gel flash column chromatography (eluent: chloroform/methanol=30/1 by volume) to obtain 3.06 g of N-[2-(1-naphthylmethyl)-6-phenylhexanoyl]-L-histidine methyl ester as a white powder.

Melting point: 45°–47° C.

To a solution of 3.05 g of N-[2-(1-naphthylmethyl)-6-phenylhexanoyl]-L-histidine methyl ester in 30 ml of methanol was added 1.6 g of hydrazine monohydrate, and the mixture was stirred for 4 hours at room temperature. The reaction mixture was concentrated under reduced pressure, and water was added to the residue. The aqueous solution was extracted with ethyl acetate, the organic layer was washed with water, dried over anhydrous magnesium sulfate, and concentrated under reduced pressure to obtain 2.92 g of N-[2-(1-naphtylmethyl)-6-phenylhexanoyl]-L-histidine hydrazide as a white powder.

Melting point: 74°–75° C.

REFERENCE EXAMPLE 20

L-Histidyl-L-leucinol.2p-tolunesulfonic acid salt

To a suspension of 10.0 g of L-histidine methyl ester dihydrochloride in 200 ml of dry chloroform were added 18.4 ml of a triethylamine and 10.2 g of 4-methoxybenzyloxycarbonylazide under cooling, and the mixture was stirred for 16 hours at 0° C. The reaction mixture was concentrated under reduced pressure, and a 5% aqueous sodium bicarbonate solution was added to the residue. The mixture was extracted with ethyl acetate. The organic layer was washed with water, dried over anhydrous magnesium sulfate, and concentrated under reduced pressure. The residue was purified by silica gel flash column chromatography (eluent: chloroform/methanol=10/1 by volume) to obtain 11.0 g of N-(4-methoxybenzyloxycarbonyl)-L-histidine methyl ester as a yellow oil.

To a solution of 10.9 g of the ester compound obtained in 112 ml of methanol was added 9.9 ml of hydrazine monohydrate, and the mixture was stirred for 4 hours at room temperature. The reaction mixture was concentrated under reduced pressure. The residue was washed with ethanol and dried under reduced pressure below 40° C. to obtain 4.9 g of N-(4-methoxybenzyloxycarbonyl)-L-histidine hydrazide as a white powder.

To a suspension of 4.10 g of the hydrazide obtained in 25 ml of N,N-dimethylformamide were successively added 8.6 ml of a dry 5.1 N-hydrogen chloride in N,N-dimethylformamide solution and 2.0 ml of isoamyl nitrite at −20° C. After disappearance of the hydrazide compound, the reaction mixture was cooled to −30° C. and neutralized with 5.9 ml of triethylamine to prepare a solution of N-(4-methoxybenzyloxycarbonyl)-L-histidine azide.

The solution was added to a solution of 1.57 g of L-leucinol and 1.67 ml of triethylamine in 38 ml of dry N,N-dimethylformamide under ice-cooling, and the mixture was stirred for 16 hours. The reaction mixture was concentrated under reduced pressure, and a 5% aqueous sodium bicarbonate solution was added to the residue. The mixture was extracted with ethyl acetate, and the organic layer was washed with water, dried over anhydrous magnesium sulfate, and concentrated under reduced pressure to obtain 3.70 g of N-(4-methoxybenzyloxycarbonyl)-L-histidyl-L-leucinol as a white powder.

To a solution of 3.6 g of the leucinol obtained in 100 ml of methanol was added 3.1 g of anhydrous p-toluenesulfonic acid, and mixture was hydrogenated over 355 mg of a 10% palladium/charcoal under a hydrogen atmosphere at room temperature. After filtration of the catalyst, the filtrate was concentrated under reduced pressure to obtain 4.6 g of bis(p-toluenesulfonic acid) of L-histidyl-L-leucinol as a white powder.

Melting points: 205°–209° C.

$Rf_1$ value: 0.21.

IR (KBr): $\nu co$ 1660 cm$^{-1}$.

NMR (CDCl$_3$) δ: 0.86(t, 6H, J=6.1 Hz), 1.27(t, 2H, J=7.1 Hz), 1.55–1.65(m, 1H), 2.29(s, 6H), 3.17(d, 2H, J=5.6 Hz), 3.25(d, 2H, J=5.5 Hz), 3.8–3.9(m, 1H), 4.05–4.15(m, 1H), 7.12(d, 4H, J=8.2 Hz), 7.50(d, 4H, J=8.2 Hz), 8.16(d, 1H, J=8.2 Hz), 9.00(s, 1H).

EXAMPLE 1

N-(2-Benzyl-3-phenylpropionyl)-L-histidyl-L-leucinal

A mixture of 240 mg of 2-benzyl-3-phenylpropionic acid and 170 mg of 1,1'-carbonyldiimidazole was added to 10 ml of dry dichloromethane, and the mixture was stirred for 30 minutes at room temperature. The reaction mixture was added to a solution of 650 mg of L-histidyl-L-leucinal semicarbazone.2p-toluenesulfonic acid salt and 200 mg of N-methylmorpholine in 10 ml of dry N,N-dimethylformamide, and the mixture was stirred overnight at room temperature. The reaction mixture was concentrated under reduced pressure, and a 5% aqueous sodium bicarbonate solution was added to the residue. The mixture was extracted with ethyl acetate, and the organic layer was dried over anhydrous magnesium sulfate, and concentrated under reduced pressure. The residue was purified by silica gel flash column chromatography (eluent: dichloromethane/methanol=10/1 by volume) to obtain 162 mg of N-(2-benzyl-3-phenylpropionyl)-L-histidyl-L-leucinal semicarbazone as a white powder.

Melting point: 111°–115° C.

$Rf_1$ value: 0.54.

MS: MH+, 532.

To a solution of 160 mg of the semicarbazone obtained in 5 ml of methanol were added 0.5 ml of 1N-hydrochloric acid and 0.5 ml of a 37 wt% formaldehyde solution under ice-cooling under an argon atmosphere. The mixture was stirred for 1 hour at room temperature. After completion of the reaction, the reaction mixture was neutralized by adding a 5% aqueous sodium bicarbonate solution. The mixture was extracted with ethyl acetate, and the organic layer was washed with water, dried over anhydrous magnesium sulfate, and concentrated under reduced pressure. The residue was purified by cephadex LH20 column chromatography (eluent; methanol) to obtain 100 mg of N-(2-benzyl-3-phenylpropionyl)-L-histidyl-L-leucinal as a white powder.

Melting point: 103°–105° C.
Rf value: 0.65.
MS: MH+, 475.

EXAMPLE 2

N-[2-(1-Naphthylmethyl)-6-phenylhexanoyl]-L-histidyl-L-leucinal

To a solution of 2.90 g of N-[2-(1-naphthylmethyl)-6-phenylhexanoyl]-L-histidine hydrazide in 70 ml of dry N,N-dimethylformamide was added 3.65 ml of a dry 5.1 N-hydrogen chloride in N,N-dimethylformamide solution at −20° C. To the mixture was added 1.33 ml of isoamyl nitrite and the mixture was stirred for 20 minutes. After disappearance of the hydrazide compound, the reaction mixture was cooled to −30° C., and then 2.73 ml of triethylamine was added to the reaction mixture to prepare a solution of N-[2-(1-naphthylmethyl)-6-phenylhexanoyl]-L-histidine azide. The azide solution was added dropwise to a solution of 1.40 g of L-leucinal semicarbazone acetic acid salt and 1.80 ml of triethylamine in 50 ml of dry N,N-dimethylformamide under ice-cooling, and the mixture was stirred for 14 hours. The reaction mixture was concentrated under reduced pressure, and a 5% aqueous sodium bicarbonate solution was added to the residue. The mixture was extracted with ethyl acetate. The organic layer was washed with water, dried over anhydrous magnesium sulfate, and concentrated under reduced pressure. The residue was purified by silica gel flash column chromatography (eluent: chloroform/methanol=20/1 by volume) to obtain 1.83 g of N-[2-(1-naphthylmethyl)-6-phenylhexanoyl]-L-histidyl-L-leucinal semicarbazone as a white powder.

Melting point: 108°–114° C.
Rf$_1$ value: 0.51.

To a solution of 1.82 g of N-[2-(1-naphthylmethyl)-6-phenylhexanoyl]-L-histidyl-L-leucinal semicarbazone in 80 ml of methanol were added 29 ml of 1N-hydrochloric acid and 7.6 ml of a 37 wt% formaldehyde solution while ice-cooling under an argon atmosphere. The mixture was stirred for 1.5 hours at room temperature, and then a 5% aqueous sodium bicarbonate solution was added to the reaction mixture. The mixture was extracted with ethyl acetate, and the organic layer was washed with a saturated sodium chloride aqueous solution, dried over anhydrous magnesium sulfate, and concentrated under reduced pressure to obtain 1.55 g of N-[2-(1-naphthylmethyl)-6-phenylhexanoyl]-L-histidyl-L-leucinal as a white powder.

Melting point: 87°–92° C.
Rf$_1$ value: 0.59.
MS: MH+, 567.

EXAMPLE 3

The following compounds were prepared in an analogous manner to that described in Example 2.

N-[4-Phenyl-2-(2-phenylethyl)butanoyl]-L-histidyl-L-leucinal:

White powder.
Melting point: 88°–92° C.
Rf$_1$ value: 0.55.
MS: MH+, 503.

N-[2-Benzyl-6-(2-naphthyl)hexanoyl]-L-histidyl-L-leucinal

White powder.
Melting point: 82°–88° C.
Rf$_1$ value: 0.55.
MS: MH+, 567.

N-[2-(1-Naphthylmethyl)-8-phenyloctanoyl]-L-histidyl-L-leucinal

White powder.
Melting point: 86°–92° C.
Rf$_1$ value: 0.59.
MS: MH+, 595.

N-[2-Benzyl-7-phenylheptanoyl]-L-histidyl-L-leucinal

White powder
Melting point: 74°–78° C.
Rf$_1$ value: 0.67.
MS: MH+, 531

N-(2-Benzyl-5-phenylpentanoyl)-L-histidyl-L-leucinal

White powder.
Melting point: 88°–92° C.
Rf$_1$ value: 0.56.
MS: MH+, 503.

EXAMPLE 4

N-[(+)-2-(1-Naphthylmethyl)-6-phenylhexanoyl]-L-histidyl-L-leucinal

A mixture of 209 mg of (+)-2-(1-naphthylmethyl)-6-phenylhexanoic acid and 411 mg of bis(p-toluenesulfonic acid) salt of L-histidyl-L-leucinal semicarbazone was dissolved in 3 ml of N,N-dimethylformamide, and then to the solution were successively added 0.163 ml of diphenylphosphoryl azide and 0.29 ml of triethylamine with stirring under ice-cooling. The reaction mixture was stirred overnight while ice-cooling. A 5% aqueous sodium bicarbonate solution was added to the reaction mixture, and the mixture was extracted with ethyl acetate. The organic layer was washed with water, dried over anhydrous magnesium sulfate, and concentrated under reduced pressure. The residue was purified by silica gel flash column chromatography (eluent: chloroform/methanol=15/1 by volume) to obtain 222 mg of N-[(+)-2-(1-naphthylmethyl)-4-phenylhexanoyl]-L-histidyl-L-leucinal semicarbazone as a white powder.

Melting point: 105°–109° C.
Rf$_1$ value: 0.51.

To a solution of 160 mg of the semicarbazone obtained in 5 ml of methanol were added 1.4 ml of a 2N-hydrochloric acid and 0.7 ml of a 37 wt% formaldehyde solution under ice-cooling under an argon atmosphere. The solution was stirred for 1 hour at room temperature, and then the reaction mixture was neutralized by adding a 5% aqueous sodium bicarbonate solution. The reaction mixture was extracted with ethyl acetate, and the organic layer was concentrated under reduced pressure to obtain 145 mg of N-[(+)-2-(1-naphthylmethyl)-6-phenylhexanoyl]-L-histidyl-L-leucinal as a white powder.

Melting point: 87°–91° C.
Rf$_1$ value: 0.59.
MS: MH+, 567.

EXAMPLE 5

The following compound was prepared in an analogous manner to that described in Example 4.

N-[(−)-2-(1-Naphthylmethyl)-6-phenylhexanoyl]-L-histidyl-L-leucinal

White powder.
Melting point: 86°–92° C.
Rf₁ value: 0.59.
MS: MH+, 567.

EXAMPLE 6

N-[(±)-2-(1-Naphthylmethylcarbamoyl)-3-phenylpropionyl]-L-histidyl-L-leucinal

A mixture of 102 mg of (±)-2-(1-naphthylmethylcarbamoyl)-3-phenylpropionic acid and 50 mg of 1,1′-carbonyldiimidazole was added to 5 ml of dichloromethane, and the mixture was stirred for 40 minutes at room temperature. The reaction mixture was added to a solution of 202 mg of L-histidyl-L-leucinal semicarbazone.2p-toluenesulfonic acid salt and 0.09 ml of triethylamine in 3 ml of N,N-dimethylformamide, and the mixture was stirred overnight at room temperature. The reaction mixture was concentrated under reduced pressure, and a 5% aqueous sodium bicarbonate solution was added to the residue. The mixture was extracted with ethyl acetate, dried and concentrated under reduced pressure. The residue was purified by preparative silica gel thin layer chromatography (developing solvent: lower layer of chloroform/methanol/water=8/3/1 by volume) to obtain 24 mg of N-[(±)-2-(1-naphthylmethylcarbamoyl)-3-phenylpropionyl]-L-histidyl-L-leucinal semicarbazone as a white powder.

To a solution of 23 mg of the semicarbazone obtained in 1 ml of methanol were added 0.4 ml of 1N-hydrochloric acid and 0.1 ml of a 37 wt% formadehyde solution under an argon atmosphere, and the mixture was stirred for 1 hour at room temperature. The reaction mixture was neutralized by adding a 5% aqueous sodium bicarbonate solution, and extracted with ethyl acetate. The organic layer was washed with water, dried over anhydrous magnesium sulfate, and then concentrated under reduced pressure to obtain 14 mg of N-[(±)-2-(1-naphthylmethylcarbamoyl)-3-phenylpropionyl]-L-histidyl-L-leucinal as a white powder.

Melting points: 90°–93° C.
Rf₁ value: 0.63.
Rf₂ value: 0.63.
MS: MH+, 568.

EXAMPLE 7

N-[(±)-2-Benzyl-3-(1-naphthylacetamido)propionyl]-L-histidyl-L-leucinal:

A mixture of 139 mg of (±)-2-benzyl-3-(1-naphthylacetamido)propionic acid and 65 mg of 1,1′-carbonyldiimidazole was added to 5 ml of dry dichloromethane, and the mixture was stirred for 1 hour at room temperature. The reaction mixture was added to a solution of 261 mg of L-histidyl-L-leucinal semicarbazone.2p-toluenesulfonic acid salt and 0.11 ml of triethylamine in 3 ml of dry N,N-dimethylformamide, and the mixture was stirred overnight at room temperature. The reaction mixture was concentrated under reduced pressure, and a 5% aqueous sodium bicarbonate solution was added to the residue. The mixture was extracted with ethyl acetate. The organic layer was dried over anhydrous magnesium sulfate, and concentrated under reduced pressure. The residue was purified by preparative silica gel thin layer chromatography (developing solvent: lower layer of chloroform/methanol/water=8/3/1 by volume) to obtain 30 mg of N-[(±)-2-benzyl-3-(1-naphthylacetamido)propionyl]-L-histidyl-L-leucinal semicarbazone as a white powder.

To a solution of 28 mg of the semicarbazone obtained in 1 ml of methanol were added 0.23 ml of a 2N-hydrochloric acid and 0.12 ml of a 37 wt% formadehyde aqueous solution under an argon atmosphere, and the mixture was stirred for 1 hour at room temperature. The reaction mixture was neutralized by adding a 5% aqueous sodium bicarbonate solution and extracted with ethyl acetate. The organic layer was washed with water, dried over anhydrous magnesium sulfate, and concentrated under reduced pressure to obtain 21 mg of N-[(±)-2-benzyl-3-(1-naphthylacetamido)propionyl]-L-histidyl-L-leucinal as a white power.

Melting point: 105°–109° C.
Rf₁ value: 0.60.
Rf₂ value: 0.49.
MS: MH+, 582.

EXAMPLE 8

N-[2-Benzylidene-3-(1-naphthylmethylcarbamoyl)propionyl]-L-histidyl-L-leucinal

A solution of 330 mg of 2-benzylidene-3-(1-naphthylmethylcarbamoyl)propionic acid, 260 mg of N,N′-disuccinimidylcarbonate and 1 ml of pyridine in 20 ml of dry acetonitrile was stirred for 3 hour at room temperature. The solution was added to a solution of 300 mg of L-histidine methyl ester dihydrochloride and 150 mg of N-methylmorpholine in 20 ml of dry N,N-dimethylformamide, and the mixture was stirred for 16 hours at 40° C. The reaction mixture was concentrated under reduced pressure, and a 5% aqueous sodium bicarbonate solution was added to the residue. The precipitates were collected by filtration to obtain 350 mg of N-[2-benzylidene-3-(1-naphthylmethylcarbamoyl)propionyl]-L-histidine methyl ester as a white powder.

To a solution of 340 mg of the ester obtained in 30 ml of methanol was added 1 g of hydrazine monohydrate, and the mixture was stirred overnight at room temperature. The reaction mixture was concentrated under reduced pressure, and a mixture of methanol and water (1:1 by volume) was added to the residue. The precipitates were collected by filtration to obtain 200 mg of N-[2-benzylidene-3-(1-naphthylmethylcarbamoyl)propionyl]-L-histidine hydrazide as a white powder.

To suspension of 160 mg of the hydrazide obtained in 5 ml of dry N,N-dimethylformamide were successively added 0.2 ml of a dry 5.35 N-hydrogen chloride in N,N-dimethylformamide solution and 60 mg of isoamyl nitrite at −20° C., and the mixture was stirred for 15 minutes. After disappearance of the hydrazide compound, the reaction mixture was cooled to −30° C., and 0.15 ml of triethylamine was added to the mixture to prepare a solution of N-[2-benzylidene-3-(1-naphthylmethylcarbamoyl)propionyl]-L-histidine azide. The solution was added dropwise to a solution of 80 mg of L-leucinal semicabazone and 0.12 ml of triethylamine in 5 ml of N,N-dimethylformamide while ice-cooling, and the mixture was stirred for 16 hours. The reaction mixture was concentrated under reduced pressure, and a 5% aqueous sodium bicarbonate solution was added to the residue. The precipitates were collected by filtration and purified by silica gel flash column chromatography (eluent: dichloromethane/methanol=10/1 by volume) to obtain 100 mg of N-[2-benzylidene-3-(1-naphthylmethylcarbamoyl)propionyl]-L-histidyl-L-leucinal semicarbazone as a white powder.

To a solution of 80 mg of the semicarbazone obtained in 5 ml of methanol were added 1 ml of a 1N-hydrochloric acid and 0.76 ml of a 37 wt% formaldehyde aqueous solution under an argon atmosphere under ice-cooling, and the mixture was stirred for 1 hour at room temperature. To the reaction mixture was added 5% aqueous sodium bicarbonate solution, and the mixture was extracted with ethyl acetate. The organic layer was washed with a saturated sodium chloride aqueous solution, dried over anhydrous magnesium sulfate, and concentrated under reduced pressure to obtain 50 mg f N-[2-benzylidene-3-(1-naphthylmethylcarbamoyl)propionyl]-L-histidyl-L-leucinal as a white powder.

Melting points: 108°–112° C.
$Rf_1$ value: 0.55.
$Rf_2$ value: 0.50.
MS: MH+, 580.

EXAMPLE 9

The following compound was prepared in an analogous manner to that described in Example 8.

N-[(±)-2-Benzyl-3-(1-naphthylmethylcarbamoyl)propionyl]-L-histidyl-L-leucinal

White powder.
Melting point: 88°–92° C.
$Rf_1$ value: 0.62.
$Rf_2$ value: 0.49.
MS: MH+, 582.

EXAMPLE 10

N-[2-(1-Naphthylmethyl)-3-(phenethylcarbamoyl)propionyl]-L-histidyl-L-leucinal (isomers A and B)

To a solution of 221 mg of (±)-2-(1-naphthylmethyl)-3-(phenethylcarbamoyl)propionic acid and 400 mg of bis-(p-toluenesulfonic acid) salt of L-histidyl-L-leucinal semicarbazone in 5 ml of dry N,N-dimethylformamide were successively added dropwise 202 mg of diphenylphosphoryl azide and 0.28 ml of triethylamine under ice-cooling, and then the mixture was stirred for 15 hours. The reaction mixture was concentrated under reduced pressure, and a 5% aqueous sodium bicarbonate solution was added to the residue. The mixture was extracted with ethyl acetate. The organic layer was washed with a saturated sodium chloride aqueous solution, dried over anhydrous magnesium sulfate, and concentrated under reduced pressure. The residue was purified by silica gel column chromatography (eluent: chloroform/methanol=10/1 by volume) to obtain 71 mg of N-[2-(1-naphthylmethyl)-3-(phenethylcarbamoyl)propionyl]-L-histidyl-L-leucinal semicarbazone (isomer A) and 166 mg of isomer B.

Isomer A

Melting point: 128°–134° C.
$Rf_1$ value: 0.33.

Isomer B

Melting point: 128°–134° C.
$Rf_1$ value: 0.40.

To a solution of 67 mg of N-[2-(1-naphthylmethyl)-3-(phenethylcarbamoyl)propionyl]-L-histidyl-L-leucinal semicarbazone (isomer A) in 3 ml of methanol were added 1.1 ml of a 1N-hydrochloric acid and 0.28 ml of a 37 wt% formaldehyde aqueous solution under an argon atmosphere under ice-cooling, the mixture was stirred for 1.5 hours at room temperature.

To the reaction mixture was added a 5% aqueous sodium bicarbonate solution, and the mixture was extracted withh ethyl acetate. The organic layer was washed with a saturated sodium chloride aqueous solution, dried over anhydrous magnesium sulfate, and concentrated under reduced pressure to obtain 43 mg of N-[2-(1-naphthylmethyl)-3-(phenethylcarbamoyl)propionyl]-L-histidyl-L-leucinal (isomer A) as a white powder.

Melting point: 101°–107° C.
$Rf_1$ value: 0.43.
$Rf_2$ value: 0.44.
MS: MH+, 596.

In the same manner as used in the preparation of isomer A, N-[2-(1-naphthylmethyl)-3-(phenethylcarbamoyl)propionyl]-L-histidyl-L-leucinal (isomer B) was prepared as a white powder.

Melting point: 98°–105° C.
$Rf_1$ value: 0.47.
$Rf_2$ value: 0.56.
MS: MH+, 596.

EXAMPLE 11

The following compounds were prepared in an analogous manner to that described in Example 10.

N-[3-(Benzylcarbamoyl)-2-(1-naphthylmethyl)propionyl]-L-histidyl-L-leucinal (isomer A)

White powder.
Melting point: 107°–112° C.
$Rf_1$ value: 0.45.
$Rf_2$ value: 0.44.
MS: MH+, 582.

N-[3-(Benzylcarbamoyl)-2-(1-naphthylmethyl)propionyl]-L-histidyl-L-leucinal (isomer B)

White powder.
Melting point: 105°–110° C.
$Rf_1$ value: 0.49.
$Rf_2$ value: 0.55.
MS: MH+, 582.

N-{3-[2-(3-Indolyl)ethylcarbamoyl]-2-(1-naphthylmethyl)propionyl}-L-histidyl-L-leucinal (isomer A)

White powder.
Melting point: 132°–137° C.
$Rf_1$ value: 0.50.
$Rf_2$ value: 0.49.
MS: MH+, 635.

N-{3-[2-(3-Indolyl)ethylcarbamoyl]-2-(1-naphthylmethyl)propionyl}-L-histidyl-L-leucinal (isomer B)

White powder.
Melting point: 131°–141° C.
$Rf_1$ value: 0.52.
$Rf_2$ value: 0.56.
MS: MH+, 635.

EXAMPLE 12

N-[(±)-2-(1-Naphthylmethyl)-5-phenyl-4-pentenoyl]-L-histidyl-L-leucinal

To a solution of 190 mg of (±)-2-(1-naphthylmethyl)-5-phenyl-4-pentenoic acid and 400 mg of bis(P-toluenesulfonic acid) salt of L-histidyl-L-leucinal semicarbazone in 7 ml of N,N-dimethylformamide were successively added 0.16 ml of diphenylphosphoryl azide and 0.28 ml of triethylamine under ice-cooling, and the mixture was stirred overnight. To the reaction mixture was added a 5% aqueous sodium bicarbonate solution, and the mixture was extracted withh ethyl acetate and washed with water. The organic layer was dried over anhydrous magnesium sulfate and concentrated under reduced pressure. The residue was purified by silica gel flash column chromatography (eluent: chloroform/methanol=15/1 by volume) to obtain 151 mg of N-[(±)-2-(1-naphthylmethyl)-5-phenyl-4-pentenoyl]-L-histidyl-L-leucinal semicarbazone as a white powder.

To a solution of 140 mg of the semicarbazone obtained in 7 ml of methanol were added 3 ml of a 1N-hydrochloric acid and 0.73 ml of 37 wt% formaldehyde solution, and the mixture was stirred for 2 hours at room temperature. The reaction mixture was neutralized by adding a 5% aqueous sodium bicarbonate solution. The mixture was extracted with ethyl acetate. The organic layer was concentrated under reduced pressure to obtain 120 mg of N-[(±)-2-(1-naphthylmethyl)-5-phenyl-4-pentenoyl]-L-histidyl-L-leucinal as a white powder.

Melting point: 92°–96° C.
$Rf_1$ value: 0.59.
$Rf_2$ value: 0.48.
MS: $MH^+$, 551.

EXAMPLE 13

The following compounds were prepared in an analogous manner to that described in Example 12.

N-[(±)-2-(1-Naphthylmethyl)-4-phenethoxybutyryl]-L-histidyl-L-leucinal

White powder.
Melting point: 70°–75° C.
$Rf_1$ value: 0.58.
$Rf_2$ value: 0.48.
MS: $MH^+$, 583.

N-[(±)-5-Benzoyl-2-(1-naphthylmethyl)valeryl]-L-histidyl-L-leucinal

White powder.
Melting point: 84°–89° C.
$Rf_1$ value: 0.60.
$Rf_2$ value: 0.47.
MS: $MH^+$, 581.

N-[(±)-2-(1-Naphthylmethyl)-7-phenyl-4,6-heptadienoyl]-L-histidyl-L-leucinal

White powder.
Melting point: 104°–107° C.
$Rf_1$ value: 0.54.
$Rf_2$ value: 0.60.
MS: $MH^+$, 577.

N-[(±)-2-(1-Naphthylmethyl)-5-phenoxyvaleryl]-L-histidyl-L-leucinal

White powder.
Melting point: 91°–94° C.
$Rf_1$ value: 0.69.
$Rf_2$ value: 0.47.
MS: $MH^+$, 569.

EXAMPLE 14

N-[2-(1-Naphthylmethyl)-3-(phenethylcarbamoyl)propionyl]-L-histidyl-L-leucinol (isomers A and B)

To a solution of 121 mg of (±)-2-(1-naphthylmethyl)-3-(phenethylcarbamoyl)propionic acid and 200 mg of L-histidyl-L-leucinol.2p-toluenesulfonic acid salt in 5 ml of N,N-dimethylformamide were successively added 0.09 ml of diphenylphosphoryl azide and 0.15 ml of triethylamine while ice-cooling, and the mixture was stirred overnight. To the reaction mixture was added a 5% aqueous sodium bicarbonate solution, and the mixture was extracted with ethyl acetate. The organic layer was washed with water, dried over anhydrous magnesium sulfate, and concentrated under reduced pressure. The residue was purified by preparative silica gel thin layer chromatography (developing solvent: lower layer of chloroform/methanol/water=8/3/1 by volume) to obtain 44 mg of N-[2-(1-naphthylmethyl)-3-(phenethylcarbamoyl)propionyl]-L-histidyl-L-leucinol (isomer A) and 75 mg of isomer B as a white powder, respectively.

Isomer A

Melting point: 96°–99° C.
$Rf_1$ value: 0.50.
$Rf_2$ value: 0.42.
MS: $MH^+$, 598.

Isomer B

Melting point: 90°–95° C.
$Rf_1$ value: 0.53.
$Rf_2$ value: 0.50.
MS: $MH^+$, 598.

EXAMPLE 15

The following compounds were prepared in an analogous manner to that described in Example 14.

N-[3-(Benzylcarbamoyl)-2-(1-naphthylmethyl)propionyl]-L-histidyl-L-leucinol (isomer A)

White powder.
Melting point: 107°–112° C.
$Rf_1$ value: 0.46.
$Rf_2$ value: 0.47.
MS: $MH^+$, 584.

N-[3-(Benzylcarbamoyl)-2-(1-naphthylmethyl)propionyl]-L-histidyl-L-leucinol (isomer B)

White powder.
Melting point: 105°–110° C.
$Rf_1$ value: 0.38.
$Rf_2$ value: 0.38.
MS: $MH^+$, 584.

N-[2-(1-Naphthylmethyl)-3-(phenylcarbamoyl)propionyl]-L-histidyl-L-leucinol (isomer A)

White powder.
Melting point: 118°–122° C.
$Rf_1$ value: 0.41.
$Rf_2$ value: 0.51.
MS: $MH^+$, 570.

N-[2-(1-Naphthylmethyl)-3-(phenylcarbamoyl)propionyl]-L-histidyl-L-leucinol (isomer B)

White powder.
Melting point: 120°–126° C.
$Rf_1$ value: 0.35.
$Rf_2$ value: 0.38.
MS: $MH^+$, 570.

N-{3-[2-(3-Indolyl)ethylcarbamoyl]-2-(1-naphthylmethyl)propionyl}-L-histidyl-L-leucinol (isomer A)

White powder.

Melting point: 108°-115° C.
Rf$_1$ value: 0.42.
Rf$_2$ value: 0.46.
MS: MH+, 637.

N-{3-[2-(3-Indolyl)ethylcarbamoyl]-2-(1-naphthylmethyl)propionyl}-L-histidyl-L-leucinol (isomer B)

White powder.
Melting point: 108°-115° C.
Rf$_1$ value: 0.35.
Rf$_2$ value: 0.35.
MS: MH+, 637.

N-[(±)-2-(1-Naphthylmethyl)-5-phenoxyvaleryl]-L-histidyl-L-leucinol

White powder.
Melting point: 91°-95° C.
Rf$_1$ value: 0.57.
Rf$_2$ value: 0.49.
MS: MH+, 571.

N-[(±)-2-(1-Naphthylmethyl)-4-phenethoxybutyryl]-L-histidyl-L-leucinol

White powder.
Melting point: 55°-62° C.
Rf$_1$ value: 0.53.
Rf$_2$ value: 0.49.
MS: MH+, 585.

N-[(±)-2-(1-Naphthylmethyl)-6-phenylhexanoyl]-L-histidyl-L-leucinol

White powder.
Melting point: 81°-83° C.
Rf$_1$ value: 0.58.
Rf$_2$ value: 0.52.
MS: MH+, 569.

N-[(±)-2-(1-Naphthylmethyl)-5-phenylvaleryl]-L-histidyl-L-leucinol

White powder.
Melting point: 88°-92° C.
Rf$_1$ value: 0.67.
Rf$_2$ value: 0.49.
MS: MH+, 555.

N-[(±)-2-(1-Naphthoxy)-6-phenylhexanoyl]-L-histidyl-L-leucinol

White powder.
Melting point: 65°-70° C.
Rf$_1$ value: 0.60.
Rf$_2$ value: 0.55.
MS: MH+, 571.

N-[(±)-5-Benzoxy-2-(1-naphthylmethyl)valeryl]-L-histidyl-L-leucinol

White powder.
Melting point: 73°-78° C.
Rf$_1$ value: 0.65.
Rf$_2$ value: 0.48.
MS: MH+, 583.

N-[(±)-2-(1-Naphthylmethyl)-5-phenyl-4-pentenoyl]-L-histidyl-L-leucinol

White powder.
Melting point: 87°-91° C.
Rf$_1$ value: 0.61.
Rf$_2$ value: 0.48.
MS: MH+, 553.

N-[(±)-2-(1-Naphthylmethyl)-7-phenyl-4,6-heptadienoyl]-L-histidyl-L-leucinol

White powder.
Melting point: 98°-103° C.
Rf$_1$ value: 0.49.
Rf$_2$ value: 0.50.
MS: MH+, 579.

N-[2-(1-Naphthylmethylene)-3-(phenethylcarbamoyl)propionyl]-L-histidyl-L-leucinol White powder.
Melting point: 92°-96° C.
Rf$_1$ value: 0.51.
Rf$_2$ value: 0.47.
MS: MH+, 596.

EXAMPLE 16

N-[2-(1-naphthylmethyl)-3-(3-phenylpropylamino)propionyl]-L-histidyl-L-leucinol (isomers A and B)

To a solution of 360 mg of (±)-3-[N-carbobenzoxy-N-(3-phenylpropyl)amino]-2-(1-naphthylmethyl)propionic acid and 450 mg of bis(p-toluenesulfonic acid) salt of L-histidyl-L-leucinol in 4 ml of dry N,N-dimethylformamide were added 0.2 ml of diphenylphosphoryl azide and 0.35 ml of triethylamine under ice-cooling, and the mixture was stirred for 15 hours. The reaction mixture was concentrated under reduced pressure, and a 5% aqueous sodium bicarbonate solution was added to the residue. The mixture was extracted with ethyl acetate. The organic layer was washed with a saturated sodium chloride aqueous solution, dried over anhydrous magnesium sulfate, and concentrated under reduced pressure. The residue was purified by silica gel column chromatography (eluent: chloroform/methanol=10/1 by volume) to obtain 300 mg of N-{(±)-3-[N-carbobenzoxy-N-(3-phenylpropyl)]amino-2-(1-naphthylmethyl)propionyl}-L-histidyl-L-leucinol as a white powder.

Melting point: 66°-70° C.
Rf$_1$ value: 0.51.
MS: MH+, 718.

A solution of 176 mg of the leucinol obtained and 0.5 ml of a 1N-hydrochloric acid in 10 ml of methanol was hydrogenated over 50 mg of a 10% palladium/charcoal under a hydrogen atmosphere at room temperature. After filtration of the catalyst, the filtrate was concentrated under reduced pressure to obtain 144 mg of a white powder. To 50 mg of the white powder obtained was added a 50% aqueous sodium bicarbonate solution, and the mixture was extracted with ethyl acetate. The organic layer was washed with a saturated sodium chloride aqueous solution, dried over anhydrous magnesium sulfate, and concentrated under reduced pressure. The residue was purified by preparative silica gel thin layer chromatography (developing solvent: lower layer of chloroform/methanol/water=8/3/1 by volume) to obtain 17 mg of N-[2-(1-naphthylmethyl)-3-(3-phenylpropylamino)propionyl]-L-histidyl-L-leucinol (isomer A) as a white powder.

Melting point: 72°-76° C.
Rf$_1$ value: 0.23.
Rf$_2$ value: 0.17.
MS: MH+, 584.

EXAMPLE 17

N-[2-(1-naphthylmethyl)-3-(phenethylcarbamoyl)propionyl]-L-histidyl-L-phenylalaninol (isomer A)

To a suspension of 1.00 g of (±)-2-(1-naphthylmethyl)-3-(phenethylcarbamoyl)propionic acid and 0.67 g of L-histidine methyl ester dihydrochloride in 8 ml of N,N-dimethylformamide were added 0.72 ml of diphenylphosphoryl azide and 1.27 ml of triethylamine under ice-cooling, and the mixture was stirred for 16 hours. The reaction mixture was concentrated under reduced pressure, and a 5% aqueous sodium bicarbonate solution was added to the residue. The mixture was extracted with ethyl acetate. The organic layer was washed with water, dried over anhydrous magnesium sulfate, and concentrated under reduced pressure. The residue was purified by silica gel flash column chromatography (eluent: chloroform/methanol=15/1 by volume) to obtain 1.36 g of N-[(±)-2-(1-naphthylmethyl)-3-(phenethylcarbamoyl)propionyl]-L-histidine methyl ester.

To a solution of 712 mg of the ester obtained in 4.5 ml of methanol was added 0.49 g of hydrazine monohydrate, and the mixture was stirred for 4 hours at room temperature. The reaction mixture was concentrated under reduced pressure, and the residue was washed with ethanol and dried under reduced pressure below 40° C. to obtain 275 mg of N-[(±)-2-(1-naphthylmethyl)3-(phenethylcarbamoyl)propionyl]-L-histidine hydrazide as a white powder.

To a suspension of 120 mg of the hydrazide obtained in 2.0 ml of N,N-dimethylformamide were successively added 0.2 ml of a dry 5.1 N-hydrogen chloride in N,N-dimethylformamide solution and 0.05 ml of isoamyl nitrite at −20° C. with stirring. After disappearance of the hydrazide compound, the reaction mixture was cooled to −30° C., and neutralized by adding 0.15 ml of triethylamine to prepare a solution of N-[(±)-2-(1-naphthylmethyl)-3-(phenethylcarbamoyl)propionyl]-L-histidine azide. The solution was added dropwise to a solution of 103 mg of L-phenylalaninol.p-toluenesulfonic acid salt and 0.05 ml of triethylamine in 1.0 ml of dry N,N-dimethylformamide while ice-cooling, and the mixture was stirred for 16 hours. The reaction mixture was concentrated under reduced pressure.

A 5% aqueous sodium bicarbonate solution was added to the residue and the mixture was extracted with ethyl acetate. The organic layer was washed with water, dried over anhydrous magnesium sulfate, and concentrated under reduced pressure. The residue was purified by preparative silica gel thin layer chromatography (developing solvent: lower layer of chloroform/methanol/water=8/3/1 by volume) to obtain 63 mg of N-[2-(1-naphthylmethyl)-3-(phenethylcarbamoyl)propionyl]-L-histidyl-L-phenylalaninol (isomer A).

White powder.
Melting point: 106°–109° C.
$Rf_1$ value: 0.66.
$Rf_2$ value: 0.38.
MS: MH+, 632.

TEST EXAMPLE 1

Human renin-sheep renin substrate reaction system in vitro

To a mixture containing 200 μl of a 125 mM pyrophosphate buffer (pH 7.4), 25 μl of a 20 mM aqueous solution of L-phenylalanyl-L-alanyl-L-proline as an angiotension converting enzyme inhibitor, 50 μl of semipurified sheep renin substrate (4400 ng angiotensin I/ml) 50 μl of dimethyl sulfoxide solution of a dipeptide of the present invention and 150 μl of deionized water was added 25 μl of purified human renin (20–30 ng angiotensin I/hr). The mixture was incubated for 15 minutes on a water bath at 37° C., and the reaction mixture was allowed to stand for 5 minutes on a water bath at 100° C. to stop the reaction. After cooling, 200 μl of the solution was taken up and the amount of angiotensin I produced by the addition of renin was determined by radioimmunoassay. The inhibitory effect was calculated by the following equation.

$$\text{Inhibition (\%)} = \frac{\text{Amount of angiotensin I in control} - \text{Amount of angiostensin I in a mixture containing a compound of this invention}}{\text{Amount of angiotensin I in control}} \times 100$$

As a control, the same procedure as above was carried out by using 50 μl of dimethyl sulfoxide alone in place of the 50 μl of dimethyl sulfoxide solution containing a dipeptide of the present invention.

The molar concentration which produced 50% inhibition ($IC_{50}$) was calculated from the inhibition value obtained, and the results are shown below.

| Compound | $IC_{50}$ (molar concentration) |
|---|---|
| N—(2-benzyl-3-phenylpropionyl)-L—histidyl-L—leucinal | $1.1 \times 10^{-6}$ |
| N—[4-phenyl-2-(2-phenethyl)-butanoyl]-L—histidyl-leucinal | $3.5 \times 10^{-6}$ |
| N—[2-(1-naphthylmethyl)-6-phenyl-hexanoyl]-L—histidyl-L—leucinal | $1.4 \times 10^{-7}$ |
| N—[2-benzyl-6-(2-naphthyl)hexanoyl]-L—histidyl-L—leucinal | $3.4 \times 10^{-6}$ |
| N—[2-(1-naphthylmethyl)-8-phenyl-octanoyl]-L—histidyl-L—leucinal | $4.2 \times^{-7}$ |
| N—(2-benzyl-7-phenylheptanoyl)-L—histidyl-L—leucinal | $2.0 \times 10^{-6}$ |
| N—(2-benzyl-5-phenylpentanoyl)-L—histidyl-L—leucinal | $2.6 \times^{-6}$ |
| N—[(+)-2-(1-naphthylmethyl)-6-phenyl-hexanoyl]-L—histidyl-L—leucinal | $8.8 \times 10^{-8}$ |
| N—[(-)-2-(1-naphthylmethyl)-6-phenyl-hexanoyl[-L—histidyl-L—leucinal | $4.6 \times 10^{-7}$ |
| N—[(±)-2-(1-naphthylmethylcarbamoyl)-3-phenylpropionyl]-L—histidyl-L—leucinal | $8.2 \times 10^{-6}$ |
| N—[(±)-2-benzyl-3-(1-naphthylacetamido)-propionyl]-L—histidyl-L—leucinal | $7.6 \times 10^{-6}$ |
| N—[2-benzylidene-3-(1-naphthylmethyl-carbamoyl)propionyl]-L—histidyl-L—leucinal | $3.8 \times 10^{-6}$ |
| N—[(±)-2-benzyl-3-(1-naphthylmethyl-carbamoyl)propionyl]-L—histidyl-L—leucinal | $7.2 \times 10^{-6}$ |
| N—[2-(1-naphthylmethyl)-3-(phenethyl-carbamoyl)propionyl]-L—histidyl-L—leucinal (isomer A) | $4.1 \times 10^{-8}$ |
| N—[-(1-naphthylmethyl)-3-phenethyl-carbamoyl)propionyl]-L—histidyl-L—leucinal (isomer B) | $4.2 \times 0\ 10^{31\ 7}$ |
| N—[3-(benzylcarbamoyl)-2-(1-naphthyl-methyl) propionyl]-L—histidyl-L—leucinal (isomer A) | $7.0 \times 10^{-8}$ |
| N—[3-(benzylcarbamoyl)-2-(1-naphthyl-methyl(propionyl]-L—histidyl-L—leucinal (isomer B) | $4.9 \times 10^{-6}$ |
| N—{3-[-(3-indolyl)ethylcarbamoyl]-2-(1-naphthylmethyl)propionyl}-L—histidyl-L—leucinal (isomer A) | $1.3 \times 10^{31\ 7}$ |

-continued

| Compound | IC$_{50}$ (molar concentration) |
|---|---|
| N—{3-[2-(3-indolyl)ethylcarbamoyl)-2-(1-naphthylmethyl)propionyl}-L—histidyl-L—leucinal (isomer B) | $9.2 \times 10^{317}$ |
| N—[(±)-2-(1-naphthylmethyl)-5-phenyl-4-pentenoyl]-L—histidyl-L—leucinal | $2.2 \times 10^{-7}$ |
| N—{(±)-2-(1-naphthylmethyl)-7-phenyl-4,6-heptadienoyl]-L—histidyl-L—leucinal | $4.4 \times 10^{-7}$ |
| N—[(±)-2-(1-naphthylmethyl)-4-phenethoxybutyryl]-L—histidyl-L—leucinal | $7.5 \times 10^{-8}$ |
| N—[(±)-5-benzoyl-2-(1-naphthyl-methyl(valeryl]-L—histidyl-L—leucinal | $1.9 \times 10^{-7}$ |
| N—[(±)-2-(1-naphthylmethyl)-5-phenoxyvaleryl]-L—histidyl-L—leucinal | $1.8 \times 10^{317}$ |
| N—[2-(1-naphthylmethyl)-3-(phenethylcarbamoyl)propionyl]-L—histidyl-L—leucinol (isomer A) | $7.4 \times 10^{-6}$ |
| N—[2-(1-naphthylmethyl)-3-(phenethylcarbamoyl)propionyl]-L—histidyl-L—leucinol (isomer B) | $2.5 \times 10^{-5}$ |
| N—[3-(benzylcarbamoyl)-2-(1-naphthylmethyl)propionyl]-L—histidyl-L—leucinol (isomer A) | $1.9 \times 10^{-5}$ |
| N—[3-(benzylcarbamoyl)-2-(1-naphthylmethyl)propionyl]-L—histidyl-L—leucinol (isomer B) | $2.7 \times 10^{-5}$ |
| N—[2-(1-naphthylmethyl)-3-(phenylcarbamoyl)propionyl]-L—histidyl-L—leucinol (isomer A) | $6.5 \times 10^{-5}$ |
| N—[2-(1-naphthylmethyl)-3-(phenylcarbamoyl)propionyl]-L—histidyl-L—leucinol (isomer B) | $1.8 \times 10^{-5}$ |
| N—{3-[2-(3-indolyl)ethylcarbamoyl]-2-(1-naphthylmethyl)propionyl}-L—histidyl-L—leucinol (isomer A) | $2.8 \times 10^{-5}$ |
| N—{3-[2-(3-indolyl)ethylcarbamoyl]-2-(1-naphthylmethyl)propionyl}-L—histidyl-L—leucinol (isomer B) | $6.6 \times 10^{-6}$ |
| N—[(±)-2-(1-naphthylmethyl)-5-phenoxyvaleryl]-l-histidyl-L—leucinol | $2.6 \times 10^{-5}$ |
| N—[(±)-2-(1-naphthylmethyl)-4-phenethoxybutyl]-L—histidyl-L—leucinol | $1.5 \times 10^{-5}$ |
| N—](+)-2-(1-naphthylmethyl)-6-phenyl-hexanoyl]-L—histidyl-L-leucinol | $5.4 \times 10^{-6}$ |
| N—[(±)-2-(1-naphthylmethyl(-5-phenyl-valeryl]-L—histidyl-L—leucinol | $1.3 \times 10^{-5}$ |
| N—[(±)-2-(1-naphthoxy)-6-phenyl-haxanoyl]-L—histidyl-L—leucinol | $7.6 \times 10^{-5}$ |
| N—[(±)-5-benzoyl-2-(1-naphthyl-methyl)valeryl]-L—histidyl-L—leucinol | $1.3 \times 10^{-5}$ |
| N—[(±)-2(1-naphthylmethyl)-5-phenyl-4-pentenoyl]-L—histidyl-L—leucinol | $2.7 \times 10^{-6}$ |
| N—[(±)-2-(1-naphthylmethyl)-7-phenyl-4,6-heptadienoyl]-L—histidyl-L—leucinol | $1.2 \times 10^{-5}$ |
| N—[2-(1-naphthylmethylene)-3-(phenethylcarbamoyl)propionyl]-L—histidyl-L—leucinol | $6.9 \times 10^{-5}$ |
| N—[2-(1-naphthylmethyl)-3-(3-phenyl-propylamino)propionyl]-L—histidyl-L—leucinol (isomer A) | $4.7 \times 10^{-5}$ |
| N—[2-(1-naphthylmethyl)-3-(phenethylcarbamoyl(propionyl]-L—histidyl-L—phenylalaninol (isomer A) | $9.1 \times 10^{-5}$ |

TEST EXAMPLE 2

Depressive effect in marmosets

The experiment was carried out by using common marmosets as described in K. G. Hofbauer et al., Clinical and Experimental Hypertension-Theory and Practice, Vol A5, Nos 7 & 8 (1983), pages 1237–1247.

Furosemide was orally administered three times to common marmosets at 15 mg per kilogram per day every other day to create a high renin state. The operation was performed according to the method used by K. G. Hofbauer et al., and blood pressure of conscious marmosets was measured 2 days after the last administration of furosemide.

Measurement of blood pressure

Male common marmosets weighing 350 g and 280 g were lightly anesthetized by Ketamine hydrochloride (Ketalar ®, 10 to 20 mg/kg i.m.), and their femoral artery and vein was exposed. Catheters being filled with a heparin solution was subcutaneously inserted into the femoral vein and the femoral artery from the tail. After suturing of the opened part, the marmosets were placed on a heated mat. After complete recovery from the anesthesia, a dipeptide of the present invention (100 mg/kg) was orally administered through a soft catheter.

The arterial catheter was connected to a pressure transducer and blood pressure was recorded on the polygraph. The results obtained are shown below.

TABLE I

| Compound | Time after administration | Blood pressure (mm Hg) |
|---|---|---|
| Control | — | 100.4 |
| N—[2-(1-naphthylmethyl)-3-(phenethylcarbamoyl)-propionyl]-L—histidyl-leucinal | 60 min. | 98.2 |
| | 120 min. | 88.0 |
| | 180 min. | 87.6 |
| | 300 min. | 96.5 |
| | 420 min. | 101.2 |

TABLE II

| Compound | Time after administration | Blood pressure (mm Hg) |
|---|---|---|
| Control | — | 106.7 |
| N—[2-(1-naphthylmethyl)-3-(phenethylcarbamoyl)-propionyl]-L—histidyl-l leucinol | 60 min. | 97.7 |
| | 120 min. | 89.5 |
| | 180 min | 95.3 |
| | 300 min. | 97.4 |
| | 420 min. | 99.0 |

What is claimed is:

1. A peptide represented by formula (I)

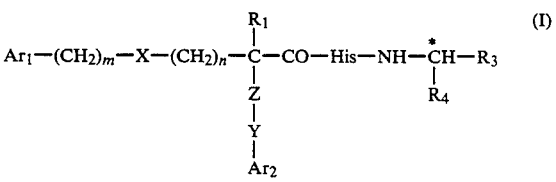

wherein His represents an L-histidyl group, Ar$_1$ represents a phenyl group, a naphthyl group or an indolyl group, Ar$_2$ represents a phenyl group or a naphthyl group, X represents a chemical bond, —NHCO—, —CO—, —CH$_2$—, —NH—, —O— or —(CH=CH-)$_p$—wherein p is 1 or 2, Z represents an oxygen atom or

in which $R_2$ represents a hydrogen atom or combines with $R_1$ to form a chemical bond, m and n, which may be the same or different, each represents an integer of from 0 to 3, provided that when X is a chemical bond, the sum of n plus m is from 1 to 6, and when X is not a chemical bond, the sum of n plus m is from 1 to 4, Y represents a chemical bond when X is not a chemical bond, or, when X is a chemical bond, an alkylene group having from 1 to 3 carbon atoms, $R_1$ represents a hydrogen atom or combines with $R_2$ to form a chemical bond, $R_3$ represents a formyl group or a hydroxymethyl group, $R_4$ represents an isobutyl group or a benzyl group, and C represents an L-configuration carbon atom; or a pharmaceutically acceptable salt thereof.

2. A peptide as in claim 1 represented by formula

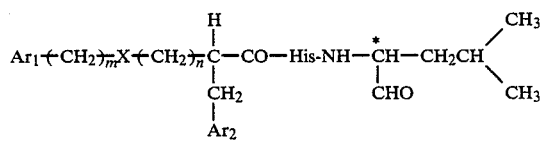

wherein $Ar_1$, m, X, n, $Ar_2$, His and C* have the same meanings as defined in claim 1.

3. A peptide as in claim 1 represented by the formula

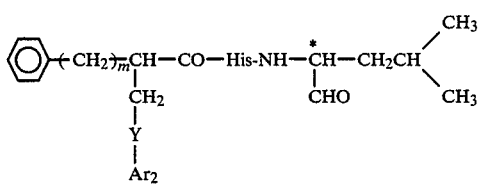

wherein $Ar_2$, m, Y, His and C* have the same meanings as defined in claim 1.

4. A peptide as in claim 2 represented by the formula

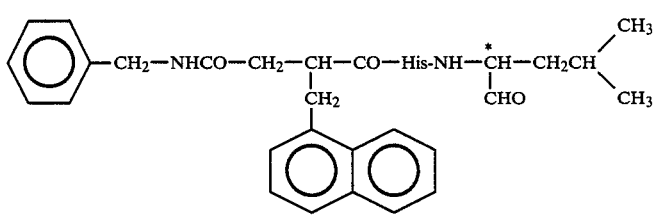

wherein His and C* have the same meanings as defined in claim 2.

5. A peptide as in claim 2 represented by the formula

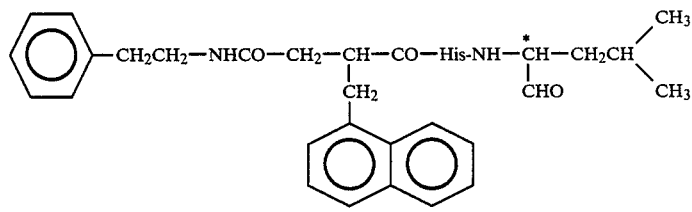

wherein His and C* have the same meanings as defined in claim 2.

6. A peptide as in claim 2 represented by the formula

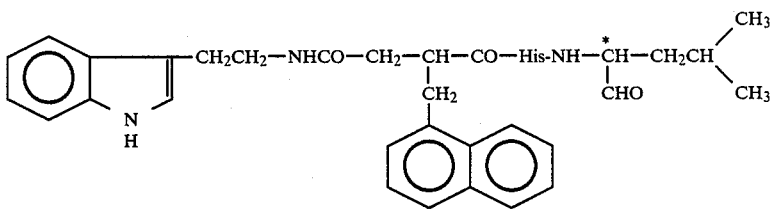

wherein His and C* have the same meanings as defined in claim 2.

7. A peptide as in claim 2 represented by the formula

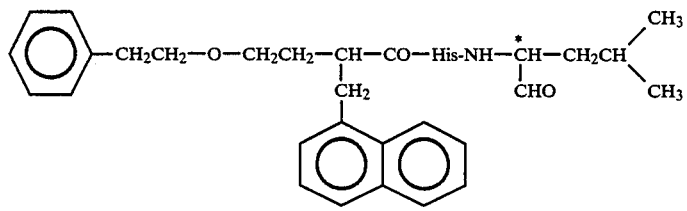

wherein His and C* have the same meanings as defined in claim 2.

8. A peptide as in claim 2 represented by the formula

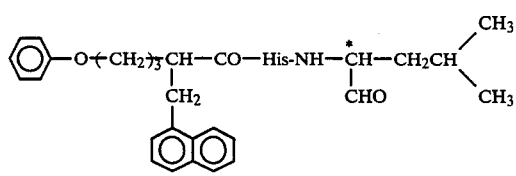

wherein His and C* have the same meanings as defined in claim 2.

9. A peptide as in claim 2 represented by the formula

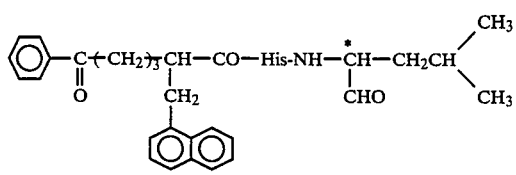

wherein His and C* have the same meanings as defined in claim 2.

10. A peptide as in claim 2 represented by the formula

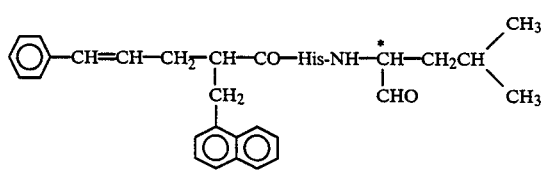

werein His and C* have the same meanings as defined in claim 2.

11. A peptide as in claim 2 represented by the formula

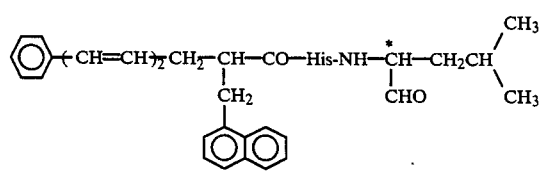

wherein His and C* have the same meanings as defined in claim 2.

12. A peptide as in claim 3 represented by the formula

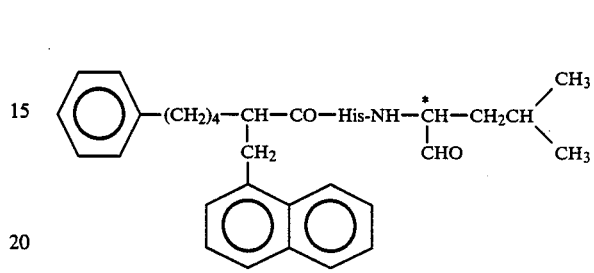

wherein His and C* have the same meanings as defined in claim 3.

13. A peptide as in claim 3 represented by the formula

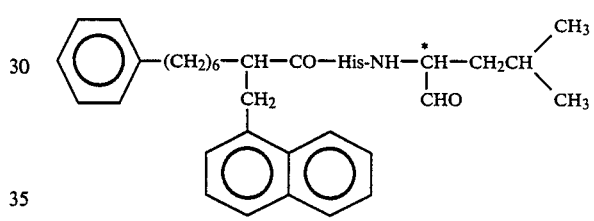

wherein His and C* have the same meanings as defined in claim 3.

14. A pharmaceutical composition for the treatment of hypertension by oral administration, containing, as an active ingredient, a peptide represented by formula (I)

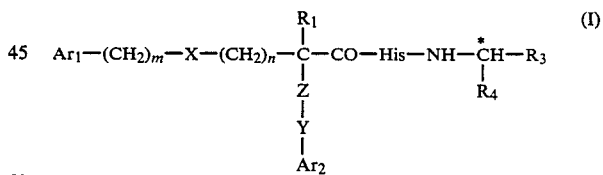

wherein His represents an L-histidyl group, $Ar_1$ represents a phenyl group, a naphthyl group, or an indolyl group, $Ar_2$ represents a phenyl group or a naphthyl group, X represents a chemical bond, —NHCO—, —CO—, —CH$_2$—, —NH—, —O— or —(CH=CH-)$_p$—, wherein p is 1 or 2, Z represents an oxygen atom or $$\begin{array}{c} R_2 \\ | \\ -CH- \end{array}$$

in which $R_2$ represents a hydrogen atom or combines with $R_1$ to form a chemical bond, n and m, which may be the same or different, each represents an integer of from 0 to 3, provided that when X is a chemical bond, the sum of n plus m is from 1 to 6, and when X is not a chemical bond, the sum of n plus m is from 1 to 4, Y represents a chemical bond when X is not a chemical bond, or, when X is a chemical bond, an alkylene group having from 1 to 3 carbon atoms, $R_1$ represents a hydrogen atom or combines with $R_2$ to form a chemcial bond, $R_3$ represents a formyl group or a hydroxymethyl group, $R_4$ represents an isobuyl group or a benzyl group, and C* represents an L-configurational carbon atom; or a pharmaceutically acceptable salt thereof; in an amount in the range of from about 5 mg to about 5000 mg per day per mammalian body in combination with a pharmaceutically acceptable carrier or diluent.

15. A pharmaceutical composition for the treatment of hypertension by parenteral administration, containing, as an active ingredient, a peptide represented by formula (I)

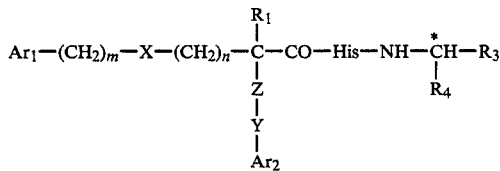

wherein His represents an L-histidyl group, $Ar_1$ represents a phenyl group, a naphthyl group, or an indolyl group, $Ar_2$ represents a phenyl group or a naphthyl group, X represents a chemical bond, —NHCO—, —CO—, —CH$_2$—, —NH—, —O— or —(CH=CH-)$_p$—, wherein p is 1 or 2, Z represents an oxygen atom or

in which $R_2$ represents a hydrogen atom or combines with $R_1$ to form a chemical bond, m and n, which may be the same or different, each represents an integer of from 0 to 3, provided that when X is a chemical bond, the sum of n plus m is from 1 to 6, and when X is not a chemical bond, the sum of n plus m is from 1 to 4, Y represents a chemical bond, or, when X is a chemical bond, an alkylene group having from 1 to 3 carbon atoms, $R_1$ represents a hydrogen atom or combines with $R_2$ to form a chemical bond, $R_3$ represents a formyl group or a hydroxymethyl group, $R_4$ represents an isobuyl group or a benzyl group, and C* represents an L-configurational carbon atom; or a pharmaceutically acceptable salt thereof; in an amount in the range of from about 1 mg to 1000 mg per day per mammalian body in combination with a pharmaceutically acceptable carrier or diluent.

16. A method for treating hypertension which comprises administering a therapeutically effective hypertension reducing amount of a peptide represented by formula (I)

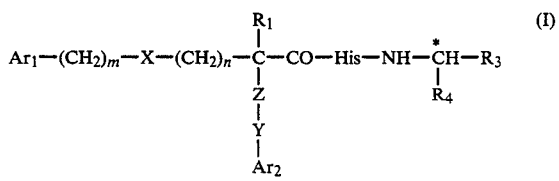

wherein His represents an L-histidyl group, $Ar_1$ represents a phenyl group, a naphthyl group, or an indolyl group, $Ar_2$ represents a phenyl group or a naphthyl group, X represents a chemical bond, —NHCO—, —CO—, —CH$_2$—, —NH—, —O— or —(CH=CH-)$_p$—, wherein p is 1 or 2, Z represents an oxygen atom or

in which $R_2$ represents a hydrogen atom or combines with $R_1$ to form a chemical bond, m and n, which may be the same or different, each represents an integer of from 0 to 3, provided that when X is a chemical bond, the sum of n plus m is from 1 to 6, and when X is not a chemical bond, the sum of n plus m is from 1 to 4, Y represents a chemical bond, or, when X is a chemical bond, an alkylene group having from 1 to 3 carbon atoms, $R_1$ represents a hydrogen atom or combines with $R_2$ to form a chemical bond, $R_3$ represents a formyl group or a hydroxymethyl group, $R_4$ represents an isobutyl group or a benzyl group, and C* represents an L-configurational carbon atom; or a pharmaceutically acceptable salt thereof.

* * * * *